(12) United States Patent
Hemmerling et al.

(10) Patent No.: US 8,133,913 B2
(45) Date of Patent: Mar. 13, 2012

(54) SUBSTITUTED INDENO [1,2-B]INDOLE DERIVATIVES AS NOVEL INHIBITORS OF PROTEIN KINASE CK2 AND THEIR USE AS TUMOR THERAPEUTIC AGENTS, CYTOSTATICS AND DIAGNOSTIC AIDS

(75) Inventors: Hans-Jorg Hemmerling, Mettmann (DE); Claudia Gotz, Saarbrucken (DE); Joachim Jose, Dusseldorf (DE)

(73) Assignee: Heinrich-Heine Universitat Dusseldof, Dusseldorf (DE)

( * ) Notice: Subject to any disclaimer, the term of this patent is extended or adjusted under 35 U.S.C. 154(b) by 0 days.

(21) Appl. No.: 12/444,349

(22) PCT Filed: Oct. 4, 2007

(86) PCT No.: PCT/EP2007/008624
§ 371 (c)(1),
(2), (4) Date: Nov. 20, 2009

(87) PCT Pub. No.: WO2008/040547
PCT Pub. Date: Apr. 10, 2008

(65) Prior Publication Data
US 2010/0056599 A1  Mar. 4, 2010

(30) Foreign Application Priority Data
Oct. 4, 2006  (DE) .......................... 10 2006 047 231

(51) Int. Cl.
*A61K 31/403* (2006.01)
*C07D 209/58* (2006.01)

(52) U.S. Cl. ........................................ 514/410; 548/420
(58) Field of Classification Search .................. 548/420; 514/410
See application file for complete search history.

(56) References Cited

U.S. PATENT DOCUMENTS
2003/0125369 A1  7/2003 Wierzbicki et al.

FOREIGN PATENT DOCUMENTS
EP   0 266 887 A   12/2002
WO   WO 90/15799 A  12/1990

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
Protein Kinase [online], [retrieved on Sep. 8, 2008]. Retrieved from the internet, URL; http://en.wikipedia.org/wiki/Protein_kinase>.*
Bullington, et al. J. Org. Chem. 1993, 58, 4833-4836.*
International Search Report PCT/EP2007/008624, Date of Completion Feb. 21, 2008, Date of Mailing Mar. 5, 2008, Authorized Officer M. Kollmannsberger 3 pages.
Sarno et al: "Features and potentials of ATP-site directed CK2 inhibitors," Biochimica Et Biophysica Acta (BBA)-Proteins & Proteomics, Elsevier, vol. 1754, No. 1-2, Dec. 2005,pp. 263-270, XP005214215, ISSN: 1570-9639.
Sarno Stefania et al: Biochemical and three-dimensional-structural study of the specific inhibition of protein kinase CK2 by (5-oxo-5,6-dihydroindolo-(1-2-a_q uinazolin-7-yl) acetic acid (IQA). Biochemical Journal, vol. 374, No. 3, Sep. 15, 2003, pp. 639-646, XP002470109 ISSN: 0264-6021.

* cited by examiner

*Primary Examiner* — Shawquia Young
(74) *Attorney, Agent, or Firm* — Millen, White, Zelano & Branigan, P.C.

(57) ABSTRACT

Synthesis of novel substituted indeno[1,2-b]indole derivatives of the type of 5,6,7,8-tetrahydroindeno[1,2-b]indole-9,10-diones and 5H-indeno[1,2-b]indole-6,9,10-triones, which show pronounced inhibition of the human protein kinase CK2, and the use thereof as active ingredients in medicaments and/or drug products in particular for the treatment of neoplastic diseases.

43 Claims, No Drawings

SUBSTITUTED INDENO [1,2-B]INDOLE DERIVATIVES AS NOVEL INHIBITORS OF PROTEIN KINASE CK2 AND THEIR USE AS TUMOR THERAPEUTIC AGENTS, CYTOSTATICS AND DIAGNOSTIC AIDS

The present invention relates to compounds of structure I, IA and II, to a process for the synthesis thereof and to pharmaceutical compositions comprising one or more of these compounds. The invention further relates to the use of these compounds for the manufacture of a medicament for the treatment of tumors and/or cancer and inflammatory disorder.

Malignant tumor diseases represent, after cardiovascular disorders, the second commonest cause of death in humans. Men are moreover affected somewhat more frequently than women. The incidence rate is of the order of 350 (men) and 250 (women) per 100 000 population per year based on the world population, whereas the mortality rate is about 170 (men) and 100 (women) per 100 000 population around the world. The immense number of those affected which results therefrom makes it clear that there is a need to develop effective therapeutic agents for neoplastic diseases. Neoplastic diseases are notable for a greatly increased cell proliferation, and inhibiting this cell proliferation by an active ingredient present in a medicament is a starting point for tumor therapy which is acknowledged around the world. Such active ingredients present in a medicament are characterized in that they prolong the survival of the patient, inhibit the increased cell proliferation associated with the neoplasm, or bring about a recession of the neoplasm. Research in this area primarily aims at developing medicaments and active ingredients which can be employed for human therapy. In this connection, compounds are often investigated on small mammals, e.g. mice, for antineoplastic activity, and it is attempted to predict therefrom activity against specific neoplastic diseases not only in these or closely related animals, but also in humans.

The protein kinase CK2 belongs together with CK1, glycogen synthasekinase and the cyclin-dependent kinases to a group of second messenger-independent kinases (1). It is able to phosphorylate Ser/Thr residues in a predominantly acidic environment. CK2 is a highly conserved kinase found from yeast to humans. It normally undertakes its tasks as ATP/GTP phosphotransferase as heterotetramer consisting of two catalytic α or α' subunits and two regulatory α subunits (2). Besides this heterotetrameric form, however, the individual subunits are present in the cell also in free form or bound to other cellular molecules. There have recently been increasing indications that CK2 is able even in this form to undertake crucial regulatory functions (3). Both as holoenzyme and as separate subunits it possibly influences transcription through the binding to nucleic acids, the activities of other molecules relevant to proliferation (p53, p21$^{WAF1}$, PP2A, mos, raf, Topoisomerase II) through binding thereto, and thus also the growth of cells (4). Whereas this function is independent of the ability to transfer phosphate groups, the most prominent task of CK2 always remains its enzymatic activity. To date, more than 160 substrates derived from a wide variety of tasks in cellular events are known. Among them there are molecules necessary for replication, transcription and translation, molecules incorporated into signal transduction chains, proto-oncogenes (mdm2) and growth suppressors (p53). It has been demonstrated for a number of these substrates that their activities are altered after phosphorylation by CK2. It can be inferred from its substrates and the influence it has on their activities that CK2 also has an influence on the growth of cells. If, for example, antibodies against CK2 or antisense oligonucleotides are injected into cells, growth arrest occurs at particular stages of the cell cycle (5-7). CK2 activity is evidently expressly required for the $G_0/G_1$, $G_1/S$ transitions and for the progression of the S phase. Recent work has additionally demonstrated that it is needed for progression through the G2 and M phase. Over expression of the catalytic subunit results in enhanced proliferation of cells, whereas overexpression of the regulatory subunit results in a serious growth defect associated with shrinkage of the cell. During embryotic development of organisms there is observed to be a tissue- and time-specific expression and activity of CK2, suggesting importance in the differentiation of cells. Recent findings indicate that CK2 is involved not only in regulating proliferation but also in inducing programmed cell death (apoptosis) (8).

Besides the importance of the protein kinase CK2 for cell proliferation and the survival of cells, there have been increasing indications recently that the enzyme is involved in the neoplastic transformation of cells and the development and progression of cancer (9, 10). Abnormally raised concentrations of the CK2 enzyme can be detected in a large number of different tumors. These include inter alia prostate cancer (11), breast cancer (12), lung cancer (13) and other cancers (14) of humans. It has also been possible to verify direct involvement of the CK2 protein kinase in malignant transformation in various animal models (15, 16). The results of these investigations and others indicate that the CK2 protein kinase is a very promising starting point for antineoplastic active ingredients (17).

Despite the unambiguous indications that CK2 is involved in malignant transformation and the development and progression of tumors, at present only a few highly active inhibitors of the enzyme are available (18, 19). These include emodin (20), 4,5,6,7-tetrabromo-1-H-benzotriazole (TBB) (21), 2-dimethylamino-4,5,6,7-tetrabromo-1H-benzimidazole (DMAT) (22), (5-oxo-5,6-dihydroindolo[1,2-a]quinoxalin-7-yl)acetic acid (IQA) (23) and ellagic acid (24). Besides the moderate activity ($IC_{50}$ for emodin: 2.0 μM, TBB: 0.9 μM), these are notable for the fact that their activity was investigated predominantly on the rat enzyme and not on the human one, and that owing to their physicochemical properties, they are unsuitable as active ingredient in a medicament, especially for oral administration.

It has been shown that CK2 may be a target for chronic inflammatory disorders, especially glomerulonephritis (26) and lupus erythematosus (27).

Indeno[1,2-b]indoles have been claimed many times: as antioxidants and radical scavengers (Sainsbury et al., EP-404536-A1), as estrogen antagonists (Miller et al. U.S. Pat. No. 6,107,292), as potassium channel openers (Antane et al. US Pat. Appl. 2001/0047026 A1), as inhibitors of topoisomerase II (Wierzbicki et al. U.S. Pat. No. 6,627,650), 4b,5,9b,10-tetrahydroindeno[1,2-b]indoles as antioxidants (Sainsbury et al. WO 90/15799 and EP-409410-B1).

The aim of the present invention was therefore to synthesize potent inhibitors which, owing to their structure, are suitable as active ingredients for use in medicaments for the treatment of neoplastic diseases and to detect their activity through potent inhibition of the human CK2 protein kinase. A further aim of the present invention was to provide inhibitors of CK2 which can be employed for the treatment of chronic inflammatory disorders.

The compounds of the invention are notable for being novel, i.e. not previously described and claimed, and for showing a potent inhibitory effect on human CK2 protein kinase and other kinases.

The present invention describes the synthesis of novel indeno[1,2-b]indole derivatives having the general structure I, IA and II. They have an inhibitory effect on protein kinases, especially of the type of serine/threonine kinases and, in this specific embodiment, on human CK2 protein kinase.

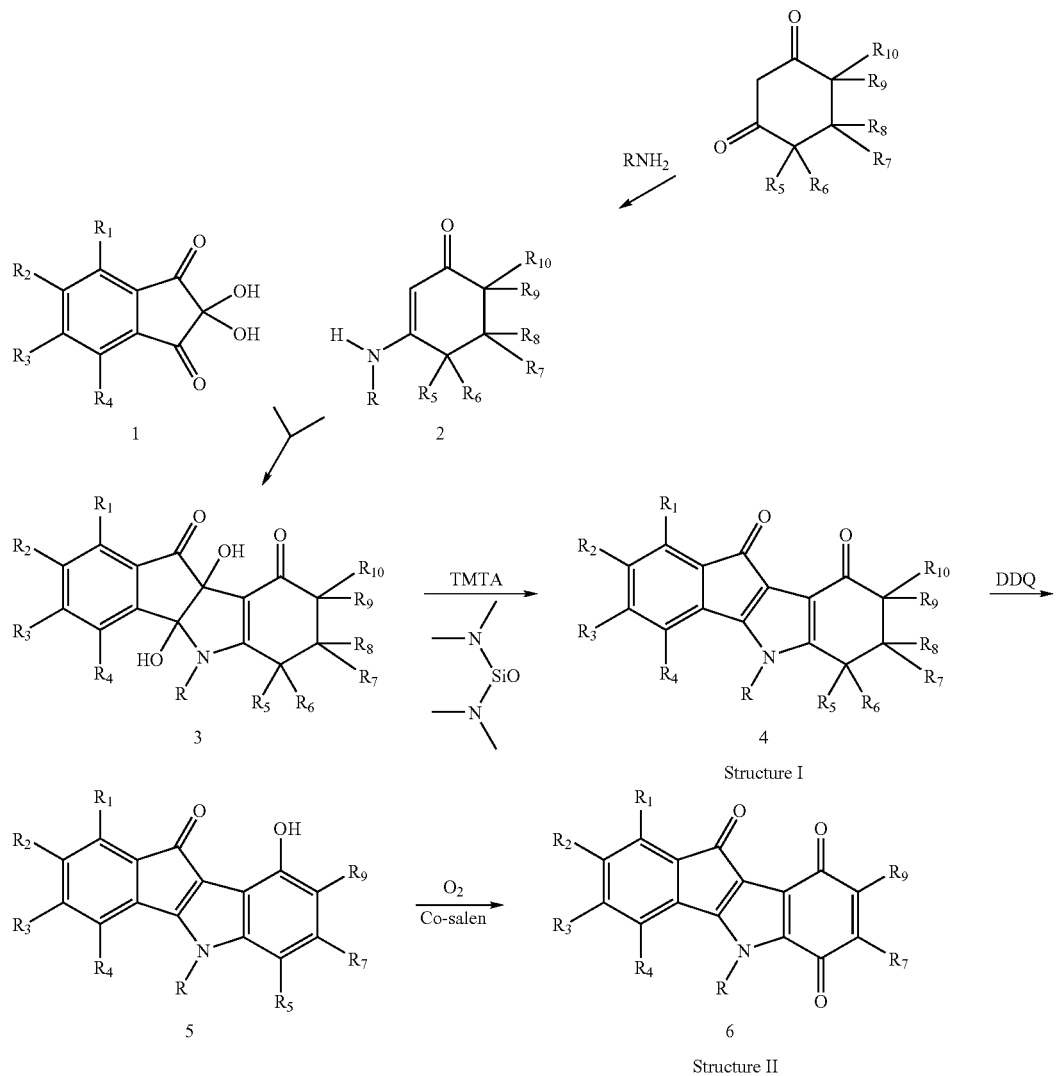

Structure I

Structure II

Synthesis of the indeno[1,2-b]indole Derivatives

One aspect of the invention is a novel, very efficient principle for synthesizing the compounds having the structure I, IA or II, starting from known and easily available precursors with very good to good yields.

1$^{st}$ Stage:

Preparation of cyclic enaminones from cyclic 1,3-diketones by reaction with ammonia or prim. amines and of indanetriones by methods known from the literature:

R and $R_1$-$R_{10}$ as described herein

2$^{nd}$ Stage:

Reaction of the enaminones 2 with indanetrione hydrate 1 to give addition compounds 3

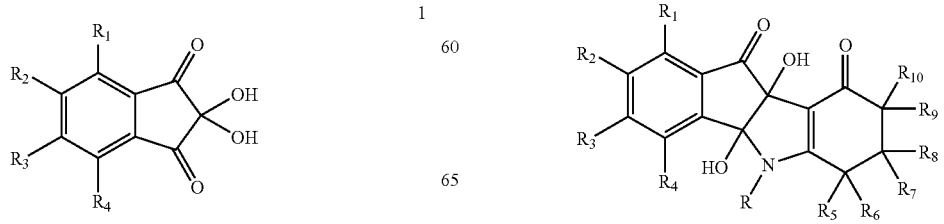

3rd Stage:

Deoxygenation of the compounds 3 with a reagent type developed by us:
N,N,N',N'-tetraalkylsulfurous diamides (TMTA: alkyl=CH$_3$, C$_2$H$_5$)

The deoxygenation is preferably carried out as described in (29).

Structure I

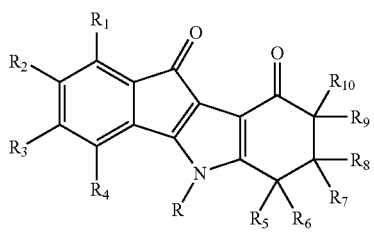

4

4th Stage:

Dehydrogenation of the compounds 4 (structure I; R$_6$=R$_8$=R$_{10}$=H) with DDQ affords 5.

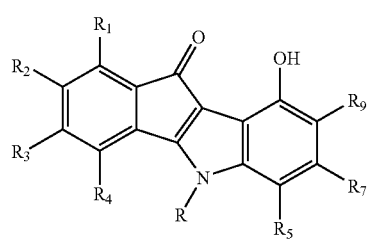

5

5th Stage:

Catalytic oxidation of compounds 5 with oxygen (R$_5$=H) leads to 6 (structure II).

Structure II

6 Stru

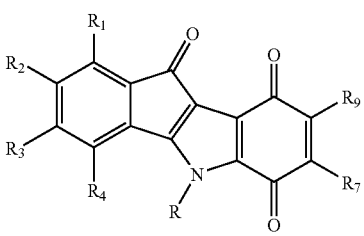

In a particularly preferred embodiment, the invention relates to the use of the novel compounds described in the invention as active ingredients in medicaments and/or pharmaceutical products for the treatment in particular of neoplastic diseases.

A further particularly preferred embodiment relates to the use of the compounds for the specific inhibition of human CK2 protein kinase.

A further embodiment is concerned with the inhibition of protein kinases in general, and specifically the inhibition of serine/threonine kinases by the compounds of the invention.

A further embodiment is concerned with the inhibition of enzymes in general, specifically human enzymes involved in the development, pathogenesis, progression and/or maintenance of a disease.

In a further particular embodiment, the invention relates to the use of the described novel compounds as active ingredients in medicaments and/or pharmaceutical products for the treatment of further disorders, especially chronically inflammatory disorders such as, for example, glomerulonephritis or/and lupus erythematosus, degenerative disorders or other disorders in which the disbalance of the regulation of cell proliferation is causally involved.

One use according to the invention of the described novel compounds is in a further particular embodiment the inhibition of protein kinases in general and specifically of serine/threonine kinases.

A further use according to the invention of the described novel compounds relates to the use thereof in diagnostic aids for investigating the part played by the CK2 protein kinase in cellular processes, in the pathogenesis of disorders or in the ontogenesis and other phenomena and relationships of developmental biology, and the investigation of the part played by protein kinases in general and serine/threonine kinases in particular in the relationships mentioned.

The present invention provides active ingredients for use in medicaments and/or pharmaceutical products for the treatment of a patient suffering in particular from a neoplastic disease, which can also be employed in combination with other previously disclosed compounds having in particular antineoplastic activity, or other active ingredients. It is possible thereby to achieve a synergistic effect and, where appropriate, even a synergistic effect going beyond expectations.

The term "patient" as used herein relates to a warm-blooded animal such as a mammal which is affected by a neoplastic disease. Animals obviously within the range of meanings of the term are cattle, horses, rats, mice, cats, dogs, sheep, goats and humans.

The term "neoplastic disease" as used herein relates to an abnormal condition or problems characterized by increased cell proliferation, cell growth or neoplasms. Neoplastic diseases for which a therapy with medicaments and/or pharmaceutical products comprising the compounds of the invention can be applied include in particular: leukemias such as acute lymphoblastic, chronic lymphocytic, acute myeloblastic and chronic myelocytic leukemia, but not restricted thereto; carcinomas such as those of the mammary gland, of the prostate, of the lung, of the neck of the uterus, of the esophagus, of the stomach, of the small bowel, of the brain, of the large bowel, but not restricted thereto; sarcomas such as osteomas, osteosarcomas, lipomas, liposarcomas, hemangiomas and hemangio-sarcomas, but not restricted thereto; melanomas, including amelotic and melanotic; and mixed types of neoplasms, such as carcinosarcomas, types of neoplasm of the lymphatic tissue, follicular reticulum neoplasms, cell sarcomas and Hodgkin's disease, but not restricted thereto. The person skilled in the art will of course appreciate that not every one of the compounds of the invention is suitable alone or in combination with other compounds having antineoplastic activity for treatment with every one of the neoplastic diseases, and can be combined and, in this case, be equally effective. Selection of the most suitable compounds and the most suitable combinations is within the ability of a person of average skill in the art and will depend on a large number of factors which include for example the assessment of results obtained in conventional animal cancer models, but also on investigation of the effect of individual compounds for the treatment of particular neoplastic diseases.

It is expected that an effective antineoplastic amount of one of the compounds of the invention will vary in the range from about 1 milligram per kilogram per day (mg/kg/day) to about 100 mg/kg/day and preferably about 0.1 to about 20 mg/kg/day.

The term "effective antineoplastic amount" as used herein relates to an amount which, after administration of a single or multiple dose to the patient for controlling the growth of the neoplasm or for prolonging the survival of the patient, has an effect which is beyond that expected in the absences of such a treatment. As used herein, "controlling growth" of the neoplasm refers to a slowing, interruption, inhibition or stopping of its growth and does not necessarily mean complete elimination of the neoplasm.

A single or multiple dose can be administered with one of the compounds of the invention alone or in combination with other compounds in particular having antineoplastic activity.

When carrying out the treatment of a patient affected by a disease described above it is possible to administer one of the compounds of the invention in any form and way making the compound bioavailable in effective amounts, including oral and parenteral routes. For example, it can be administered orally, subcutaneously, intramuscularly, intravenously, transdermally, intranasally, rectally and the like. Oral administration is generally preferred. A person skilled in the art of producing formulations can easily select the appropriate form and mode of administration depending on the particular circumstances, which include the state of the disease to be treated, the stage of the disease, the form of administration of the compound in combination with other active ingredients in particular having antineoplastic activity or alone, the selected type of joint administration and the like.

In a preferred embodiment of the present invention, the compounds of the invention are administered orally in a formulation of the following composition: compound 10 g, hydroxypropylcellulose 2 g, cereal starch 11 g, lactose 100 g, magnesium stearate 3 g and talc 3 g, in which case the ingredients in the described amounts and ratios of amounts are sufficient to produce 1000 tablets with an active ingredient content of 10 mg.

The compounds of the invention can, provided they have activity, be formulated and administered in the form of their pharmaceutically acceptable acid addition salts for the purpose of stability, convenience of crystallization, increased solubility and the like.

A further particular embodiment of the invention relates to the use of the compounds of the invention in so-called pro-drugs.

A further particular embodiment of the invention relates to the use of the compounds of the invention as precursors in further synthetic steps to improve the solubility, the bioavailability, the physicochemical properties and the like.

The invention also relates to the following specific embodiments:

EMBODIMENT 1

Compounds of Structure I and Structure II

Structure I

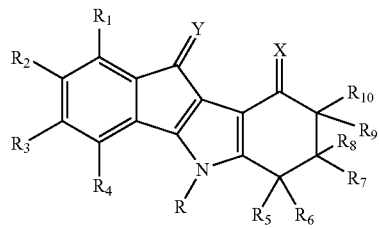

Structure II

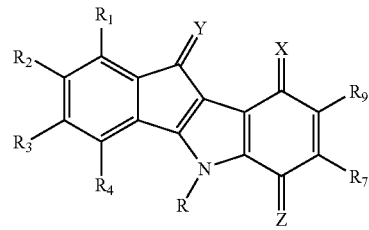

in which R can be
a hydrogen atom
an alkyl group (C1-C8) straight-chain or branched,
cycloalkyl group (C1-C8) or
alkenyl group ($C_1$-$C_8$) straight-chain or branched or
cycloalkenyl group (C1-C8) or
aryl group or
heteroaryl group,
which are optionally substituted by hydroxy, cyano, nitro, halogen, carboxy, sulfonic acid, carboxamido and thiocarboxamido groups, sulfonamide groups ($CONR_{11}R_{12}$, $CSNR_{11}R_{12}$, $SO_2NR_{11}R_{12}$ ($R_{11}$, $R_{12}$ can be identically or differently hydrogen atoms, straight-chain or branched alkyl groups (C1-C8) or cycloalkyl groups (C2-C8)), amino groups $NR_{13}R_{14}$ ($R_{13}$, $R_{14}$ can be identically or differently straight-chain or branched alkyl groups (C1-C8 or cycloalkyl groups (C2-C8) or together with the nitrogen atom carrying them forming a nitrogen heterocycle, alkoxycarbonyl group $COOR_{15}$ ($R_{15}$: straight-chain or branched alkyl groups (C1-C8) or cycloalkyl groups (C1-C8), optionally substituted by hydroxy, halogen, cyano, nitro, carboxy, carbamoyl and thiocarbamoyl groups, sulfamoyl groups $CO(NR_{16}R_{17}$, $CSNR_{16}R_{17}$, $SO_2NR_{16}R_{17}$, ($R_{16}$, $R_{17}$ may be identically or differently hydrogen atoms, straight-chain or branched alkyl groups (C1-C8) or cycloalkyl groups (C2-C8)), amino groups $NR_{18}R_{19}$ ($R_{18}$, $R_{19}$ identically or differently may be hydrogen, linear or branched alkyl groups (C1-C8 or cycloalkyl groups (C2-C8) or together with the nitrogen atom carrying them forming a nitrogen heterocycle), an aminoalkyloxyalkyl $NR_{20}R_{21}$ ($R_{20}$, $R_{21}$ may be identically or differently hydrogen atoms, straight-chain or branched alkyl groups (C1-C8), or together with the nitrogen atom carrying them forming a nitrogen heterocycle) are substituted,
a nitrogen function $NR_{22}R_{23}$
($R_{22}$, $R_{23}$ may be hydrogen or identical or different straight-chain or branched alkyl groups (C1-C8) or cycloalkyl groups (C2-C8), aryl groups, heteroaryl groups), alkoxy groups $OR_{24}$, ($R_{24}$ may be a straight-chain or branched alkyl group), optionally substituted by hydroxy, halogen, cyano, nitro, carboxy, carboxamido and thiocarboxamido groups, sulfonamido groups ($CO(NR_{25}R_{26}$, $CSNR_{25}R_{26}$, $SO_2NR_{25}R_{26}$, (with $R_{25}R_{26}$ identically or differently may be hydrogen, straight-chain or branched alkyl groups (C1-C8), aryl groups, heteroaryl groups or together with the nitrogen atom carrying them forming a nitrogen heterocycle), alkoxycarbonyl group (C1-C8) $COOR_{27}$ (with $R_{27}$ straight-chain or branched alkyl groups (C1-C8, cycloalkyl groups, aryl groups, heteroaryl groups, optionally substituted by hydroxy, halogen, cyano, nitro, carboxy, carboxamido and thiocarboxamido groups, sulfonamido groups ($CO(NR_{28}R_{29}$, $CSNR_{28}R_{29}$, $SO_2NR_{28}R_{29}$, (with $R_{28}R_{29}$ may be identically or differently hydrogen, straight-chain or branched alkyl groups (C1-C8), or together with the nitrogen atom carrying them forming a nitrogen heterocycle), an aminoalkyloxyalkyl $NR_{30}R_{31}$, ($R_{30}$, $R_{31}$ may be identical or different straight-chain or branched alkyl groups (C1-C8) or together with the nitrogen atom carrying them form a nitrogen heterocycle, or aryl or heteroaryl groups), an oxygen function $OR_{32}$ ($R_{32}$ may be hydrogen or a straight-chain or branched alkyl group (C1-C8) or cycloalkyl group (C2-C8), optionally substituted by hydroxy, halogen, cyano, nitro, carboxy, carbamoyl and thiocarbamoyl groups, sulfamoyl groups $CO(NR_{16}R_{17}$, $CSNR_{16}R_{17}$, $SO_2NR_{16}R_{17}$, alkoxy groups ($R_{29}$ may be a linear or branched alkyl groups (C1-C8) or cycloalkyl groups (C2-C8), an alkoxycarbonyl group, linear or branched (C1-C8) or cycloalkyl (C1-C8), an aminoalkyloxyalkyl $NR_{30}R_{31}$ ($R_{30}$, $R_{31}$ may be identical or different linear or branched alkyl groups (C1-C8), or with the nitrogen atom carrying them form a nitrogen heterocycle) or aryl or heteroaryl groups).

$R_1$-$R_{10}$ may be identical or different.

Each may be a hydrogen atom, an alkyl group (C1-C8) straight-chain or branched or a cycloalkyl group (C1-C8) or an alkenyl group (C1-C8) straight-chain or branched or a cycloalkenyl group (C1-C8) or an aryl group, or a heteroaryl group, which are optionally substituted by hydroxy, cyano, nitro, halogen, carboxy, sulfonic acid, carboxamido and thiocarboxamido groups, sulfonamide groups ($CONR_{32}R_{33}$, $CSNR_{32}R_{33}$, $SO_2NR_{32}R_{33}$ ($R_{32}$, $R_{33}$ may be identically or differently hydrogen atoms, straight-chain or branched alkyl groups (C1-C8) or cycloalkyl groups (C2-C8)), amino groups $NR_{34}R_{35}$ ($R_{34}$, $R_{35}$ identically or differently may be straight-chain or branched alkyl groups (C1-C8 or cycloalkyl groups (C2-C8) or together with the nitrogen atom carrying them forming a nitrogen heterocycle, are substituted), alkoxycarbonyl group $COOR_{36}$ ($R_{36}$: straight-chain or branched alkyl groups (C1-C8) or cycloalkyl groups (C1-C8), optionally substituted by hydroxy, halogen, cyano, nitro, carboxy, carbamoyl and thiocarbamoyl groups, sulfamoyl groups $CO(NR_{37}R_{38}$, $CSNR_{37}R_{38}$, $SO_2NR_{37}R_{38}$, ($R_{37}$, $R_{38}$ may be identically or differently hydrogen atoms, straight-chain or branched alkyl groups (C1-C8) or cycloalkyl groups (C2-C8)), amino groups $NR_{39}R_{40}$ ($R_{39}$, $R_{40}$ identically or differently may be hydrogen, linear or branched alkyl groups (C1-C8 or cycloalkyl groups (C2-C8) or together with the nitrogen atom carrying them forming a nitrogen heterocycle), an aminoalkyloxyalkyl $NR_{41}R_{42}$, ($R_{41}$, $R_{42}$ may be identically or differently hydrogen atoms, straight-chain or branched alkyl groups (C1-C8), or together with the nitrogen atom carrying them forming a nitrogen heterocycle), optionally substituted by an aryl, carboxy or by an alkoxycarbonyl group, linear or branched (C1-C8).

A hydroxy group

An Acyloxycarbonyl group, $OCOR_{43}$ ($R_{43}$ may be a straight-chain or branched alkyl group (C1-C8) or cycloalkyl group or aryl group or heteroaryl group).

A carboxy group

An amino function $NR_{44}R_{45}$ in which $R_{44}R_{45}$ may be identically or differently straight-chain or branched alkyl groups (C1-C8) or cycloalkyl (C1-C8), aryl groups or heteroaryl groups, optionally substituted by an amino group $NR_{46}R_{47}$ in which $R_{46}$, $R_{47}$ may be identical or different and may be straight-chain or branched (C1-C8) alkyl groups (C1-C8) or cycloalkyl (C1-C8), aryl groups or heteroaryl groups.

An alkoxy group with straight-chain or branched alkyl groups (C1-C8) or cycloalkyl (C1-C8), aryl groups or heteroaryl groups an alkenyloxy group with straight-chain or branched alkyl groups (C1-C8) or cycloalkyl (C1-C8), aryl groups or heteroaryl groups, optionally substituted by an aryl group or an amino function $NR_{36}R_{37}$ in which $R_{36}$, $R_{37}$ may be identical or different, each of them may carry linear or branched (C1-C8) alkyl groups or cycloalkyl groups (C1-C8), or together with the nitrogen atom form a nitrogen-containing heterocycle or one of the substituents $R_1$-$R_{10}$ forms with an adjacent $R_1$-$R_{10}$ an alkylenedioxy group X may be oxygen a nitrogen function $NR_{40}$ in which $R_{40}$ may be a hydrogen atom, an alkyl group linear or branched (C1-C8) or a cycloalkyl group (C1-C8) or an aryl or an arylalkyl (C1-C8) group, in which the alkyl chain may be linear or branched. The alkyl group may optionally have one or more multiple bonds and/or be substituted by a plurality of groups which may be identical or different and may be substituted together or singly by aryl, heteroaryl, cycloalkyl (C3-C8), cyano, nitro or an amino function $NR_{41}R_{42}$ ($R_{41}$, $R_{42}$ may be identical or different alkyl groups (C1-C8), linear or branched or cycloalkyl (C1-C8) or form together with the nitrogen atom carrying them a heterocycle). Alkyl groups or cycloalkyl groups (C1-C8) may be or form with the nitrogen atom carrying them a nitrogen-containing heterocycle, optionally substituted by hydroxy, halogen, cyano, nitro, carboxy, sulfonyl, carboxamido and thiocarboxamido groups, sulfonamide groups $CONR_{37}R_{38}$, $CSNR_{37}R_{38}$, $SO_2NR_{37}R_{38}$) may be.

Y may be oxygen, a nitrogen function $NR_{48}$ in which $R_{48}$ represents a hydrogen atom, an alkyl group linear or branched (C1-C8), or an aryl or an arylalkyl (C1-C8) group, in which the alkyl chain may be linear or branched. The alkyl group may optionally have one or more multiple bonds and/or be substituted by a plurality of groups which may be identical or different and may be aryl, heteroaryl, cycloalkyl (C3-C8), cyano or an amino function $NR_{49}R_{50}$ ($R_{49}$, $R_{50}$ may be identical or different alkyl (C1-C8) or cycloalkyl groups (C2-C8, linear or branched or form with the nitrogen atom carrying them a heterocycle.

Z may be oxygen a nitrogen function $NR_{49}$ in which $R_{49}$ represents a hydrogen atom, an alkyl group straight-chain or branched (C1-C8), or an aryl or an arylalkyl (C1-C8) group, in which the alkyl chain may be straight-chain or branched. The alkyl group may optionally have one or more multiple bonds and/or be substituted by a plurality of groups which may be identical or different and may be aryl, heteroaryl, cycloalkyl (C3-C8), cyano, nitro or an amino function $NR_{49}R_{50}$ ($R_{49}$, $R_{50}$ may be identical or different alkyl (C1-C8) or cycloalkyl groups (C2-C8, linear or branched or form with the nitrogen atom carrying them a heterocycle.

Isomers mean optical isomers and geometric isomers at double bonds. The embodiment includes both mixtures of isomers and the pure isomers (diastereomers, enantiomers, e/z isomers).

Aryl groups mean phenyl, naphthyl groups which may be substituted together or singly by one or more identically or different substituents such as halogen, alkoxy, phenoxy, nitro, cyano, amino groups $NR_{43}R_{44}$ ($R_{43}R_{44}$ may be identically or different alkyl groups (C1-C8), linear or branched or cycloalkyl (C1-C8) or form with the nitrogen atom carrying them a heterocycle) or substituted by arylalkyl, and/or alkyl groups, linear or branched (C1-C8) or cycloalkyl (C1-C8) or alkylenedioxy (C1-C2), aminoalk(C1-C8)oxy groups $NR_{45}R_{46}$ ($R_{45},R_{46}$ may be identically or different alkyl groups (C1-C8), linear or branched or cycloalkyl (C1-C8) or form with the nitrogen atom carrying them a heterocycle).

Heteroaryl groups mean aromatic mono- or bicyclic ring system with 5 to 12 ring members which comprise 1-3 heteroatoms (O, N, S) which may be substituted together or singly by one or more identically or different substituents such as halogen, alkoxy, phenoxy, nitro, cyano, amino groups $NR_{43}R_{44}$ ($R_{43}R_{44}$ may be identical or different alkyl groups (C1-C8), linear or branched or cycloalkyl (C1-C8) or form with the nitrogen atom carrying them a heterocycle) or substituted by arylalkyl and/or alkyl groups, linear or branched (C1-C8) or cycloalkyl (C1-C8) or alkylenedioxy (C1-C2), aminoalk(C1-C8)oxy groups $NR_{45}R_{46}$ ($R_{45},R_{46}$ be identical or different alkyl groups (C1-C8), linear or branched or cycloalkyl (C1-C8) or form with the nitrogen atom carrying them a heterocycle).

A nitrogen-containing heterocycle means a saturated monocycle with 5-7 ring members and which comprises 1-3 heteroatoms (O, N, S).

EMBODIMENT 2

In a particularly preferred embodiment of the invention compounds according to embodiment 1 characterized in that X is an oxygen atom.

EMBODIMENT 3

In a further particularly preferred embodiment of the invention compounds according to embodiment 1 characterized in that Y is an oxygen atom.

EMBODIMENT 4

In a further particularly preferred embodiment of the invention compounds according to embodiment 1 characterized in that Z is an oxygen atom.

EMBODIMENT 5

In a further particularly preferred embodiment of the invention compounds according to embodiment 1 characterized in that X=Y=oxygen.

EMBODIMENT 6

In a further particularly preferred embodiment of the invention compounds according to embodiment characterized in that $R_5$-$R_{10}$ is hydrogen.

EMBODIMENT 7

In a further particularly preferred embodiment of the invention compounds according to embodiment 1 characterized in that X=Y=Z=oxygen.

EMBODIMENT 8

In a further particularly preferred embodiment of the invention compounds according to embodiment 1 characterized in that $R_7$=$R_9$=hydrogen.

EMBODIMENT 9

In a further particularly preferred embodiment of the invention compounds according to embodiment 1 characterized in that $R_1$-$R_{10}$ may be identical or different and are hydrogen, alkyl or alkoxy groups.

EMBODIMENT 10

In a further particularly preferred embodiment of the invention compounds according to embodiment 1 characterized in that R is a hydrogen atom, an alkyl group, linear or branched (C1-C8), an aryl group or an arylalkyl group, linear or branched (C1-C8).

EMBODIMENT 11

In a further particularly preferred embodiment of the invention the compound according to embodiment 1 (structure I) with the name (IUPAC): 5-isopropyl-5,6,7,8-tetrahydroindeno[1,2-b]indole-9,10-dione or a salt of this compound with a pharmaceutically useful acid.

EMBODIMENT 12

In a further particularly preferred embodiment of the invention the compound according to embodiment 1 (structure I) with the name (IUPAC): 5-phenethyl-5,6,7,8-tetrahydroindeno[1,2-b]indole-9,10-dione or a salt of this compound with a pharmaceutically useful acid.

EMBODIMENT 13

In a further particularly preferred embodiment of the invention the compound according to embodiment 1 (structure I) with the name (IUPAC): 5-(1-phenylethyl)-5,6,7,8-tetrahydroindeno[1,2-b]indole-9,10-dione, its isomers or a salt of this compound with a pharmaceutically useful acid.

EMBODIMENT 14

In a further particularly preferred embodiment of the invention the compound according to embodiment 1 (structure I) with the name (IUPAC): 5-phenyl-5,6,7,8-tetrahydroindeno[1,2-b]indole-9,10-dione or a salt of this compound with a pharmaceutically useful acid.

EMBODIMENT 15

In a further particularly preferred embodiment of the invention the compound according to embodiment 1 (structure II) with the name (IUPAC): 5-isopropyl-5H-indeno[1,2-b]indole-6,9,10-trione or a salt of this compound with a pharmaceutically useful acid.

EMBODIMENT 16

In a further particularly preferred embodiment of the invention the compound according to embodiment 1 (structure II) with the name (IUPAC): 5-benzyl-5,6,9,10-tetrahydroindeno[1,2-b]indole-6,9,10-trione or a salt of this compound with a pharmaceutically useful acid.

EMBODIMENT 17

In a further particularly preferred embodiment of the invention the compound according to embodiment 1 (structure II) with the name (IUPAC): 5-phenethyl-5H-indeno[1,2-b]indole-6,9,10-trione or a salt of this compound with a pharmaceutically useful acid.

EMBODIMENT 18

Compounds according to embodiment 1, characterized in that they are derived from the enolized form of structure I (with $XR_{11}$ =OR or NRR; referred to as structure IA hereinafter) and in that R corresponds to the optionally substituted alkyl, aryl, heteroaryl groups cited in embodiment 1.

EMBODIMENT 19

Use of the compounds according to embodiment 1-18 as active ingredients in medicaments and/or pharmaceutical products for the treatment in particular of neoplastic diseases.

EMBODIMENT 20

In a further particularly preferred embodiment the use of the compounds according to embodiment 1-18 for the specific inhibition of the human CK2 protein kinase.

EMBODIMENT 21

Use of the compounds according to the embodiment 1-18 for the inhibition of protein kinases in general, specifically with the inhibition of serine/threonine kinases.

EMBODIMENT 22

Use of the compounds according to embodiment 1-18 for the inhibition of enzymes in general, in particular human enzymes involved in the development, the pathogenesis, the progression and/or the maintenance of a disease.

EMBODIMENT 23

Use of the compounds according to embodiment 1-18 for employment in diagnostic aids for investigating the part played by the CK2 protein kinase in cellular processes, in the pathogenesis of diseases or in the ontogenesis and other developmental biological phenomena and relationships, and for investigating the part played by protein kinases in general and serine/threonine kinases in particular in the relationships mentioned.

EMBODIMENT 24

Use of the compounds according to embodiment 1-18 in medicaments and/or pharmaceutical products for the treatment of a patient suffering in particular from a neoplastic disease, also in combination with other previously disclosed compounds having in particular antineoplastic activity or other active ingredients.

EMBODIMENT 25

A method for the treatment of living animal organisms suffering from neoplastic diseases with compounds according to embodiment 1-18 alone or in combination.

EMBODIMENT 26

A pharmaceutical preparation, characterized in that it comprises as active ingredient compounds of the structure I, structure IA or structure II according to embodiment 1-18 alone or in combination with other active ingredients in an effective dosage and has been prepared with pharmaceutically customary additions and excipients.

The following representative examples and tables demonstrate the invention. Examples are intended to be only illustrative and are not intended to restrict the scope of the invention in any way.

Legends

Table 1 is a compilation of compounds of the invention and comparative compounds.

Table 2: $IC_{50}$ values of selected indeno[1,2-b]indoles for the human CK2 protein kinase (holoenzyme).

Table 3: Proliferation of tumor cell lines after incubation with various indeno[1,2-b]indoles.

Table 4: $IC_{50}$ values of the cell proliferation of selected indeno[1,2-b]indoles for various tumor cell lines.

Table 5: $IC_{50}$ values [µM] of selected indeno[1,2-b]indoles for various human protein kinases.

EXAMPLE 1

5-Isopropyl-5,6,7,8-tetrahydroindeno[1,2-b]indole-9, 10-dione 4b

The structures of the compounds were verified in this and in examples 2 to 26 by spectral data (NMR, IR, MS) and microanalyses, and in a few cases also by X-ray structure.

$1^{st}$ stage: 3-Isopropylaminocyclohex-2-enone after

Equimolar amounts of isopropylamine and cyclohexane-1,3-dione were dissolved in benzene and heated with addition of p-toluenesulfonic acid to boiling with a water trap. After the trapping of water was complete, the mixture was thoroughly washed with water, the solvent was stripped off, and the residue was recrystallized.

2nd stage: 4b,9b-Dihydroxy-5-isopropyl-4b,5,6,7,8, 9b-hexahydroindeno[1,2-b]indole-9,10-dione Equimolar amounts of 3-isopropylaminocyclohex-2-enone and indanetrione hydrate (ninhydrin) were dissolved in chloroform and stirred at room temperature for 12 h. The solvent was then stripped off, and the oily residue was crystallized from acetone.

$3^{rd}$ stage: 5-Isopropyl-5,6,7,8-tetrahydroindeno[1,2-b]indole-9,10-dione 4b

The compound obtained after stage 2 (0.01 mol) were dissolved in 20 ml of N,N-dimethylformamide DMF. Addition of 5 ml of acetic acid was followed by rapid addition of 0.04 mol of N,N,N',N'-tetramethyl-sulfoximide dissolved in 5 ml of DMF. The mixture is stirred for 3 h and then added to 500 ml of water, and the precipitate which separates out is filtered off. It is dried and recrystallized.

m.p.: 201° C. (Ethyl acetate).

Microanalysis:

$C_{18}H_{19}NO_4$ (313.34) calc.*: C. 68.99; H. 6.11; N. 4.47; found: C. 68.95; H. 6.17; N. 4.52.

*calc.=calculated

4<sup>th</sup> stage: 9-Hydroxy-5-isopropyl-5H-indeno[1,2-b]indole-10-one

The compound obtained after stage 3 (1.0 g, 3.61 mMol) were dissolved in 150 ml of dioxane, and DDQ (0.91 g, 4 mMol) r dissolved in dioxane, were added. The mixture was heated at 70° C. for 4 h. After filtration, the mixture was concentrated and purified by a column chromatography on $SiO_2$/ethyl acetate.

m.p.: 182° C. (Methanol).
Microanalysis:
$C_{18}H_{15}NO_2$ (277.32) calc.: C. 77.96; H. 5.45; N. 5.05, found: C. 78.18; H. 5.66; N. 5.00.

5<sup>th</sup> stage
5-Isopropyl-5H-indeno[1,2-b]indole-6,9,10-trione 6b

The compound obtained after stage 4 (0.8 g, 2.5 mMol) was dissolved in 100 ml of DMF, 80 mg of co-salen were added, and oxygen was passed in at 70° C. After 4 h, the starting material had disappeared. The mixture was concentrated, dissolved in chloroform and purified by column chromatography ($SiO_2$/ethyl acetate).

m.p.:
Microanalysis:
$C_{20}H_{22}N_4O_2$ (350.41) calc.: C. 74.22; H. 4.50; N. 4.81; found: C. 74.03; H. 4.39; N. 4.74.

EXAMPLE 2

5-Benzyl-5,6,7,8-tetrahydroindeno[1,2-b]indole-9,10-dione

The compound is obtained in compliance with the process indicated above.
m.p.: 185° C. (ethyl acetate).
Microanalysis
$C_{22}H_{17}NO_2$ (327.38) calc.: C. 80.71; H. 5.23; N. 4.28; found: C. 80.81; H. 5.20; N. 4.24.

EXAMPLE 3

5-Benzyl 5,6,9,10-tetrahydroindeno[1,2-b]indole-6,9,10-trione 6c

The compound is obtained in compliance with the process indicated above.
m.p.: 224° C. (2-Propanol).
HRMS: calc. 339.08954; found: 339.08955.

EXAMPLE 4

5,6,7,8-Tetrahydroindeno[1,2-b]indole-9,10-dione

The compound is obtained in compliance with the process indicated above.
m.p.: 332-3° C. (Water/dioxane).
Microanalysis
$C_{15}H_{11}NO_2$ (237.25) calc.: C. 75.94; H. 4.67; N. 5.90; found: C. 75.34; H. 4.71; N. 5.93.

EXAMPLE 5

5-Phenethyl-5,6,7,8-tetrahydro-indeno[1,2-b]indole-9,10-dione 4d

The compound is obtained in compliance with the process indicated above.
m.p.: 189-90° C. (Ethyl acetate).
Microanalysis
$C_{23}H_{19}NO_2$ (341.40) calc.: C. 80.92; H. 5.61; N. 4.10; found: C. 80.92; H. 5.39; N. 4.04.

EXAMPLE 6

5-Phenethyl-5H-indeno[1,2-b]indole-6,9,10-trione 6d

The compound is obtained in compliance with the process indicated above.
m.p.: >310° C. Decomposition (ethyl acetate).
Microanalysis
$C_{23}H_{15}NO_3$ (353.11) calc.: C. 78.17; H. 4.28; N. 3.96; found: C. 77.54; H. 4.34; N. 3.89.

EXAMPLE 7

DL-5-(1-phenylethyl)-5,6,7,8-tetrahydro-indeno[1,2-b]indole-9,10-dione 4f

The compound is obtained in compliance with the process indicated above.
m.p.: 201° C. (Ethyl acetate).
Microanalysis
$C_{23}H_{19}NO_2$ (341.40) calc.: C. 80.92; H. 5.61; N. 4.10; found: C. 80.79; H. 5.74; N. 4.00.

EXAMPLE 8

5-[2-(3,4-Dimethoxyphenyl)ethyl]-5,6,7,8-tetrahydroindeno[1,2-b]indole-9,10-dione The compound is obtained in compliance with the process indicated above
m.p.: 189-90° C. (DMF/$H_2O$).
Microanalysis
$C_{25}H_{23}NO_4$ (401.45) calc.: C. 74.79; H. 5.77; N. 3.49; found: C. 74.63; H. 5.84; N. 3.37.

EXAMPLE 9

5-Phenyl-5,6,7,8-tetrahydroindeno[1,2-b]indole-9,10-dione 4g

The compound is obtained in compliance with the process indicated above
m.p.: 288° C. (Acetonitrile)
Microanalysis
$C_{21}H_{19}NO_2$ (313.35) calc.: C. 80.49; H. 4.82; N. 4.47; found: C. 80.49; H. 4.78; N. 4.43.

EXAMPLE 10

Methyl (9,10-dioxo-6,8,7,9,10-tetrahydro-7H-indeno[1,2-b]indol-5-yl)acetate

The compound is obtained in compliance with the process indicated above
m.p.: 256-7° C. (ethyl acetate)
Microanalysis
$C_{18}H_{15}NO_4$ (309.32) calc.: C. 69.89; H. 4.89; N. 4.53; found: C. 69.61; H. 4.92; N. 4.50.

EXAMPLE 11

5-(2-Dimethylaminoethyl)-5,6,7,8-tetra-hydroindeno[1,2-b]indole-9,10-dione

The compound is obtained in compliance with the process indicated above
m.p.: 178° C. (methanol)
Microanalysis
$C_{19}H_{20}N_2O_2$ (308-37) calc.: C. 74.00; H. 6.54; N. 9.08; found: C. 73.82; H. 6.68; N. 9.11.

EXAMPLE 12

5-(3-Hydroxypropyl)-5,6,7,8-tetrahydro-indeno[1,2-b]indole-9,10-dione

The compound is obtained in compliance with the process indicated above
m.p.: 241° C. (Acetonitrile)
Microanalysis
$C_{18}H_{17}NO_3$ (295.33): calc.: C. 73.20; H. 5.80; N. 4.74; found: C. 73.04; H. 5.78; N. 4.84.

EXAMPLE 13

(9,10-Dioxo-6,8,9,10-tetrahydro-7H-indeno[1,2-b]indol-5-yl)acetic acid

By hydrolysis with methanolic potassium hydroxide of the compound obtained after example 10
m.p.: 279-80° C. (decomp. above 240° C.) (DMSO/$H_2O$).
Microanalysis
$C_{17}H_{13}NO_4$ (295.29): calc.: C. 69.15; H. 4.44; N. 4.74; found: C. 69.11; H. 4.55; N. 4.74.

EXAMPLE 14

5-(2-Hydroxyethyl)-5,6,7,8-tetrahydro-indeno[1,2-b]indole-9,10-dione

The compound is obtained in compliance with the process indicated above
m.p.: 262-3° C. (DMSO/$H_2O$)
Microanalysis
$C_{17}H_{15}NO_3$ (281.31) calc.: C. 72.58; H. 5.37; N. 4.98; found: C. 72.53; H. 5.33; N. 4.96.

EXAMPLE 15

2-(9,10-Dioxo-6,8,9,10-tetrahydro-7H-indeno[1,2-b]indol-5-yl)ethyl methanesulfonic acid ester By reaction of the compound obtained after example 14 with methanesulfonyl chloride
m.p.: 230-1° C. (Acetonitrile).
Microanalysis
$C_{18}H_{17}NO_5S$ (359.40): calc.: C. 60.15; H. 4.77; N. 3.90; found: C. 60.25; H. 4.84; N. 4.03.

EXAMPLE 16

5-Ethoxypropyl-5,6,7,8-tetrahydro-indeno[1,2-b]indole-9,10-dione

The compound is obtained in compliance with the process indicated above
m.p.: 129° C. (Ethyl acetate).
Microanalysis
$C_{20}H_{21}NO_3$ (323.39) calc.: C. 74.28; H. 6.55; N. 4.33; found: C. 74.17; H. 6.64; N. 4.20.

EXAMPLE 17

5-[2-(3,4-Dimethoxyphenyl)ethyl]-5,6,7,8-tetrahydroindeno[7,2-b]indole-9,10-dione The compound is obtained in compliance with the process indicated above
m.p.: 189-90° C. (DMF/$H_2O$.
Microanalysis
$C_{25}H_{23}NO_4$ (401.45): calc.: C. 74.79; H. 5.77; N. 3.49; found: C. 74.63; H. 5.84; N. 3.37.

EXAMPLE 18

5-(4-Methoxybenzyl)-5,6,7,8-tetrahydro-indeno[1,2-b]indole-9,10-dione

The compound is obtained in compliance with the process indicated above
m.p.: 198-9° C. (Ethyl acetate).
Microanalysis
$C_{23}H_{19}NO_3$ (357.40) calc.: C. 77.29; H. 5.36; N. 3.92; found: C. 77.12; H. 4.97; N. 3.81.

EXAMPLE 19

5-Isopropyl-7-methyl-5,6,7,8-tetrahydro-indeno[1,2-b]indole-9,10-dione

The compound is obtained in compliance with the process indicated above
m.p.: 264-5° C. (Ethyl acetate).
Microanalysis
$C_{19}H_{19}NO_2$ (293.36) calc.: C. 77.79; H. 6.53; N. 4.77; found: C. 77.55; H. 6.73; N. 5.06.

EXAMPLE 20

Methyl 7-methyl-9,10-dioxo-5-phenyl-5,6,7,8,9,10-hexahydroindeno[1,2-b]indole-8-carboxylate The compound is obtained in compliance with the process indicated above
m.p.: 249-50° C. (Ethyl acetate).
Microanalysis
$C_{24}H_{19}NO_4$ (385.42) calc.: C. 74.79; H. 4.97; N. 3.63; found: C. 74.58; H. 5.21; N. 3.51.

EXAMPLE 21

Methyl 7-methyl-9,10-dioxo-5,6,7,8,9,10-hexahydroindeno[1,2-b]indole-8-carboxylate The compound is obtained in compliance with the process indicated above.
m.p.: 287° C. (DMSO/H$_2$O).
Microanalysis
C$_{18}$H$_{15}$NO$_4$ (309.32): calc.: C. 69.89; H. 4.89; N. 4.53; found: C. 69.67; H. 4.80; N. 4.35.

EXAMPLE 22

5-Benzyl-7-phenyl-5,6,7,8-tetrahydro-indeno[1,2-b]indole-9,10-dione

The compound is obtained in compliance with the process indicated above.
m.p.: 252° C. (Toluene).
Microanalysis
C$_{28}$H$_{21}$NO$_2$ (403.49) calc.: C. 83.35; H. 5.25; N. 3.47; found: C. 83.54; H. 5.27; N. 3.33.

EXAMPLE 23

5-Benzyl-7-phenyl-6,9-dihydro-5R-indeno[1,2-b]indole-6,9,10-trione

The compound is obtained in compliance with the process indicated above
m.p.: 247-8° C. (Acetonitrile).
HRMS: C$_{28}$H$_{17}$NO$_3$ calc.: 415.12085, found: 415.12111.

EXAMPLE 24

7-Methyl-5-phenethyl-5,6,7,8-tetrahydro-indeno[1,2-b]indole-9,10-dione

The compound is obtained in compliance with the process indicated above
m.p.: 228-9° C. (Acetonitrile).
Microanalysis
C$_{24}$H$_{21}$NO$_2$ (355.43): calc.: C. 81.10; H. 5.96; N. 3.94; found: C. 80.85; H. 6.07; N. 3.98

EXAMPLE 25

Ethyl 2-(9-hydroxy-10-oxo-10H-indeno[1,2-b]indol-5-yl)methanesulfonate

The compound is obtained in compliance with the process indicated above
m.p.: 188° C. (Acetonitrile).
Microanalysis
C$_{18}$H$_{15}$NO$_5$S (357.85): calc.: C. 60.49; H. 4.23; N. 3.92; found: C. 60.41; H. 4.10; N. 4.24.

EXAMPLE 26

9-Hydroxy-5-isopropyl-5H-indeno[1,2-b]indol-10-one

The compound is obtained in compliance with the process indicated above
m.p.: 182° C. (Methanol).
Microanalysis
C$_{18}$H$_{15}$NO$_2$ (277.32) calc.: C. 77.96; H. 5.45; N. 5.05; found: C. 78.18; H. 5.66; N. 5.00.

Literature on the Synthesis of the Precursors (Incorporated Herein by Reference)

Synthesis of Cyclic Enaminones

Greenhill, J. V. et al.: J. Heterocyci. Chem. 1992, 29, 1375-1383
Edafiogho, I. O. et al.: J. Med. Chem. 1992, 35, 2798-2805
Kesten, S. J. et al.: J. Med. Chem. 1992, 35, 3429-3447
Scott, K. R. et al. J. Med. Chem. 1993, 36, 1947-1955 and many others Synthesis of Substituted Indanetriones Joullie, M. M. et al. Tetrahedron 1991, 47, 8791-8830
Hark, R. R. et al.: Can. J. Chem. 2001, 79, 1632-1654
Hansen, D. B. et al.: Chem. Soc. Rev. 2005, 34, 408-417
Deoxygenation Reaction:
Synthesis of the reagent described by Dorlars, A. in Houben-Weyl: Methoden der organischen Chemie Volume 11/2, 4$^{th}$ Edition, page 737

EXAMPLE 27

IC$_{50}$ Values of Selected Compounds

TABLE 2

Inhibition of recombinant human CK2 protein kinase (holoenzyme) by selected synthesized substituted indeno[1,2-]indole derivatives.

| | Compound[1] | R[2] | Inhibition % [10 μM][3] | IC$_{50}$ [μM][4] |
|---|---|---|---|---|
| 1 | 4b | Iso-C$_3$H$_7$ | 93.4 | 0.11 |
| 2 | 4d | (CH$_2$)$_2$C$_6$H$_5$ | 67.0 | 0.82 |
| 3 | 4f | CH(CH$_3$)C6H5 | 66.0 | 4.66 |
| 4 | 4g | C$_6$H$_5$ | 60.0 | 1.44 |
| 5 | 6b | Iso-C$_3$H$_7$ | 73.3 | 5.05 |
| 6 | 6c | CH$_2$C$_6$H$_5$ | 60.0 | 1.49 |
| 7 | 6d | (CH$_2$)$_2$C$_6$H$_5$ | 70.0 | 5.74 |

1) Designation according to examples 1-26.
2) R corresponds to R in structure I or structure II with R7 and R9 being H.
3) For testing the inhibitory effect of the synthesized substituted indeno[1,2-]indole derivatives, the human CK2 protein kinase was recombinantly expressed in *E. coli* and purified to homogeneity. Expression and purification of the CK2 protein kinase and its catalytic subunit took place in accordance with the following protocol based on Guerra et al. (25). The α subunit and the β subunit of CK2 were expressed either separately starting from the pT7-7 system in BI21(DE3) or together starting from the bicistronic vector pET11d-CK2α, β. The purification procedure was the same in both cases. BL21(DE3) were transformed freshly with the appropriate constructs. The resulting colonies were transferred into a preculture and left to grow at 37° C. to saturation overnight. The following day, a main culture was set up starting from the preculture (6 l of medium/construct) and was left to grow until the $OD_{600nm}$ was 0.6. Expression of the protein was then induced by adding IPTG (1 mM). Induction for CK2 α or the holoenzyme amounted to 5-6 h at 30° C., while induction of CK2 β ran at 37° C. for 3 h. The bacteria were harvested by centrifugation at 6000 g for 10 min. The pellets can be preserved at −80° C. All purification steps were carried out at low temperature in order to avoid degradation of the enzyme. The bacteria were initially taken up in water (100 ml/10 g of bacteria) and disrupted by ultrasound (3×30 s with the ultrasonic probe, while cooling). The bacteria residues were removed by centrifugation, and the supernatant was stored as aqueous extract. The bacterial pellet was then taken up in P1500 buffer (100 ml/10 g) and extracted further by stirring at 4° C. overnight (P1500 extract). The two subunits from the two extracts were combined and dialyzed against P300 (20 mM Tris/HCl, pH 8.0, 0.3 M NaCl, 7 mM 2-mercaptoethanol, 0.2 mM PMSF). The dialyzate was loaded onto a P11 cation exchange column (phosphocellulose from Whatman, 150 ml of swollen gel) which had previously been equilibrated with P360. The subsequent chromatography was carried out with the aid of a bio-rad chromatography unit (Econo system). The column was washed with P300 until the extinction measured at 280 nm returned to its initial level. The proteins adhering to the column were eluted by applying a linear salt gradient between 300 and 1500 ME NaCl and collected in fractions (80 fractions of 7.5 ml) (flow rate 1.5 ml/min, total volume 600 ml). The CK2-containing fractions were identified by Western blot analysis with CK2-specific antibodies and an activity assay with the synthetic peptide RRRDDDSDDD. CK2 eluted approximately in the middle of the gradient at 700 mM NaCl. The fractions were combined, dialyzed against P300 and concentrated by loading once again onto a P11 matrix (about 15 ml of swollen gel). The proteins binding to the column were eluted by immediately changing the buffer system to P1500 in a volume of 20-30 ml. For the subsequent gel filtration on a Superose 6 matrix (Pharmacia, 2.6×90 cm), the fractions were concentrated to a volume of 5 ml with the aid of polyethylene glycol and then dialyzed against P1000 (20 mM Tris/HCl, pH 8.0, 1 M NaCl, 7 mM 2-mercaptoethanol, 0.2 mM PMSF). The gel filtration took place with P1000 at a flow rate of 1 ml/min and was documented by measuring the extinction at 280 nm. The eluate was collected in fractions as described above, analyzed, concentrated if necessary and dialyzed against P100 (20 mM Tris/HCl, pH 8.0, 100 mM NaCl, 7 mM 2-mercaptoethanol, 0.2 mM PMSF). The purified enzyme was stored in portions at −80° C.

For the testing, in each case about 5 ng (=5 U, where 1 U corresponds to the amount of enzyme which transfers 1 µmol of phosphate to a predefined substrate) were recombinantly expressed and purified human CK2 were pre-incubated with a final concentration of 10 µM of the compound or the same volume of DMSO as control in kinase buffer (50 mM Tris/HCl, pH 7.5, 100 mM NaCl, 10 mM $MgCl_2$, 1 mM DTT) in a total volume of 20 µl at room temperature for 10 min. The compounds were usually stored in a stock solution of 5 mM in DMSO. The reaction was started by adding 30 µl of assay buffer (25 mM Tris/HCl, pH 8.5, 150 mM NaCl, 5 mM $MgCl_2$, 1 mM DTT, 100 µM ATP, 0.19 mM substrate (synthetic peptide RRRDDDSDDD) and 0.6 µCi of [$\gamma$-$^{32}$] ATP). After incubation at 37° C. for 15 min, the complete mixture was spotted onto a type P81 ion exchange chromatography filter paper. After washing three times with an excess of phosphate (85 µM $H_3PO_4$) and then with ethanol, the filter was dried and the adhering amount of radioactivity was determined using a Packard scintillation counter. The adhering radioactivity on the filters of the DMSO controls was fixed as 100% CK2 enzyme activity, and the relationship to the activity of the enzyme on addition and preincubation with the stated compounds in the concentration of 10 µM was obtained. Each value was determined at least three times in independent experiments.

4) To determine the $IC_{50}$, the enzyme assay was carried out as described under 3) with variable final concentrations of the compounds in the concentration range from 30 µM to 0.01 µM in suitable intervals. It was possible to calculate the respective $IC_{50}$ from the calibration plot constructed in this way, which describes the linear relationship between the decadic logarithm of the concentration of compound and the percent inhibition. Each value was determined at least three times in independent experiments.

EXAMPLE 28

Proliferation of Tumor Cell Lines after Incubation with Various indeno[1,2b]indoles The $IC_{50}$ values of the cell proliferation was determined as described by Bracht et al. (28). The results are compiled in table 3.

EXAMPLE 29

$IC_{50}$ Values of the Cell Proliferation of Selected indeno[1,2,-b]indoles for Various Tumor Cell Lines The $IC_{50}$ values of the cell proliferation was determined as described by Bracht et al. (28). The results are compiled in table 4.

EXAMPLE 30

$IC_{50}$ Values [µM] of Selected indeno[1,2,-b]indoles of Various Human Protein Kinases a) Recombinant Protein Kinases The following 24 protein kinases were used to determine inhibition profiles:
AKTI1, ARK5, Aurora-A, Aurora-B, B-RAF-VE, CDK2/CycA, CDK4/CycD1, CK2-alpha1 (catalytic subunit of CK2), EGF-R, EPHB4, ERBB2, FAK, IGF1-R, SRC, VEGF-R2, VEGF-R3, FLT3, INS-R, MET, PDGFR-beta, PLK1, SAK, TIE2, COT.

All the protein kinases were expressed in Sf9 insect cells as human recombinant GST fusion proteins or His-tagged proteins by the baculovirus expression system. Kinases were purified by affinity chromatography either by GSH-agarose (Sigma) or Ni—NTH-agarose (Qiagen). The purity of the kinases was tested by SDS-PAGE/silver staining, and the identity of the kinases was verified by Western blot analysis with specific antibodies or mass spectroscopy.

b) Protein Kinase Assay

A radiometric protein kinase assay (33PanQinase® Activity Assay) was used to measure the kinase activity for the 24 protein kinases. The kinase assays were carried out in 96-well FlashPlates™ from Perkin Elmer/NEN (Boston, Mass., USA) in a reaction volume of 50 µl. The reaction mixture was pipetted in 4 steps in the following sequence:

20 µl of assay buffer
5 µl of ATP solution (in $H_2O$)
5 µl of test compound (in 10% DMSO)
10 µl of substrate/10 µl of enzyme solution (premixed)

The assays for all the enzymes contained 60 mM HEPES-NaOH, pH 7.5, 3 mM MgCl2, 3 mM MnCl2, 3 µM Na orthovanadate, 1.2 mM DTT, 50 µg/ml $PEG_{20000}$, 1 µM [$\gamma$-$^{33}$P]-ATP (about 5×10$^5$ cpm per well).

The following amounts of enzymes and substrate per well were employed for the 24 kinases:

| # | Kinase | Kinase Conc. ng/50 µl | Substrate | Substrate ng/50 µl |
|---|--------|---|---|---|
| 1 | AKT1 | 100 | GSK3(14-27) (Lot 006) | 1000 |
| 2 | ARK5 | 100 | CHKtide (Lot 002) | 1000 |
| 3 | Aurora-A | 50 | tetra(LRRWSLG) | 500 |
| 4 | Aurora-B | 50 | tetra(LRRWSLG) | 250 |
| 5 | B-RAF VE | 20 | MEK1 KM (Lot 018) | 250 |
| 6 | CDK2/CycA | 100 | Histone H1 | 125 |
| 7 | CDK4/CycD1 | 50 | Rb-CTF (Lot 011) | 500 |
| 8 | CK2-alpha1 | 200 | Casein | 200 |
| 9 | EGF-R | 25 | Poly(Glu,Tyr)4:1 | 125 |
| 10 | EPHB4 | 10 | Poly(Glu,Tyr)4:1 | 125 |
| 11 | ERBB2 | 100 | Poly(Glu,Tyr)4:1 | 125 |
| 12 | FAK | 200 | Poly(Glu,Tyr)4:1 | 125 |
| 13 | IGF1-R | 20 | Poly(Glu,Tyr)4:1 | 125 |
| 14 | SRC | 10 | Poly(Glu,Tyr)4:1 | 125 |
| 15 | VEGF-R2 | 10 | Poly(Glu,Tyr)4:1 | 125 |
| 16 | VEGF-R3 | 100 | Poly(Glu,Tyr)4:1 | 125 |
| 8 | COT | 400 | Autophosphorylation | — |
| 21 | PLK1 | 50 | CHKtide (Lot 002) | 2000 |
| 22 | SAK | 200 | p38-alphaKRKR (Lot 002) | 1000 |
| 23 | TIE2 | 006 | 200 Poly(Glu,Tyr)4:1 | 250 |
| 17 | FLT3 | SP007 | 100 Poly(Ala,Glu,Lys,Tyr)6:2:5:1 | 125 |
| 18 | INS-R | SP005 | 25 Poly(Ala,Glu,Lys,Tyr)6:2:5:1 | 125 |
| 19 | MET | SP011 | 100 Poly(Ala,Glu,Lys,Tyr)6:2:5:1 | 125 |
| 20 | PDGFR-beta | SP012 | 100 Poly(Ala,Glu,Lys,Tyr)6:2:5:1 | 125 |

The reaction mixture was incubated at 30° C. for 80 minutes. The reaction was stopped with 50 µl of 2% (v/v) $H_3PO_4$. The plates were aspirated and washed twice with 200 µl of 0.9% (w/v) NaCl. The incorporation of $^{33}Pi$ was determined using a microtiter plates scintillation counter (Microbeta Trilux, Wallac).

All the assays were carried out with a BeckmanCoulter/Sagian robot system.

The results are compiled in table 5.

Tables

TABLE 1

Synthesized indeno [1,2-b]indoles

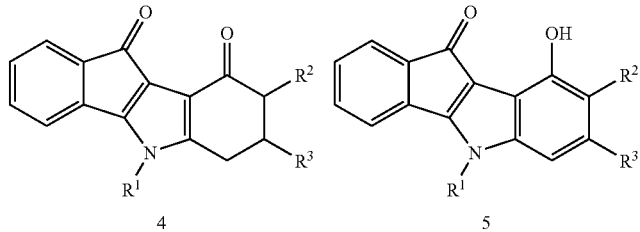

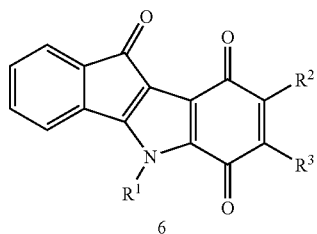

| Compound | | $R^1$ | $R^2$ | $R^3$ |
|---|---|---|---|---|
| 1 | 4a | H | H | H |
| 2 | 4b | Iso-$C_3H_7$ | H | H |
| 3 | 4c | $CH_2C_6H_5$ | H | H |
| 4 | 4d | $(CH_2)_2C_6H_5$ | H | H |

TABLE 1-continued

Synthesized indeno [1,2-b]indoles

| | Compound | R¹ | R² | R³ |
|---|---|---|---|---|
| 5 | 4e | $(CH_2)_3C_6H_5$ | H | H |
| 6 | 4f | $CH(CH_3)C_6H_5$ | H | H |
| 7 | 4g | $C_6H_5$ | H | H |
| 8 | 4h | $CH_2$-2-$C_5H_4N$ | H | H |
| 9 | 4i | $CH_2C_6H_4$-4-$OCH_3$ | H | H |
| 10 | 4j | $(CH_2)_2C_6H_3$-3,4-$(OCH_3)_2$ | H | H |
| 11 | 4k | $CH_2C_6H_5$ | H | $(CH_3)_2$ |
| 12 | 4l | H | $COOCH_3$ | $CH_3$ |
| 13 | 4m | $CH_2C_6H_5$ | $COOCH_3$ | $CH_3$ |
| 14 | 4n | $CH_2C_6H_5$ | H | $C_6H_5$ |
| 15 | 4o | $CH_2C_6H_5$ | H | $CH_3$ |
| 16 | 4p | $(CH_2)_2C_6H_5$ | H | $CH_3$ |
| 17 | 5b | Iso-$C_3H_7$ | H | H |
| 18 | 5c | $CH_2C_6H_5$ | H | H |
| 19 | 5j | $(CH_2)_2C_6H_3$-3,4-$(OCH_3)_2$ | H | H |
| 20 | 5n | $CH_2C_6H_5$ | H | $C_6H_5$ |
| 21 | 6b | Iso-$C_3H_7$ | H | H |
| 22 | 6c | $CH_2C_6H_5$ | H | H |
| 23 | 6d | $(CH_2)_2C_6H_5$ | H | H |

TABLE 2

$IC_{50}$ values of selected indeno[1,2-b]indoles for human CK2 protein kinase

| | Substance[1] | R[2] | Inhibition % [10 μM][3] | $IC_{50}$ [μM][4] |
|---|---|---|---|---|
| 1 | 4b | Iso-$C_3H_7$ | 93.4 | 0.11 |
| 2 | 4d | $(CH_2)_2C_6H_5$ | 67.0 | 0.82 |
| 3 | 4f | $CH(CH_3)C_6H_5$ | 66.0 | 4.66 |
| 4 | 4g | $C_6H_5$ | 60.0 | 1.44 |
| 5 | 6b | Iso-$C_3H_7$ | 73.3 | 5.05 |
| 6 | 6c | $CH_2C_6H_5$ | 60.0 | 1.49 |
| 7 | 6d | $(CH_2)_2C_6H_5$ | 70.0 | 5.74 |

[1] Designation as in table 1
[2] R corresponds to R in structure I or structure II, with R7 and R9 being H.

TABLE 3

Table 3: Proliferation of tumor cell lines after incubation with various indeno[1,2-b]indoles

| Compound | T/C (%) | | | | | |
|---|---|---|---|---|---|---|
| | 5637 | | SISO | | KYSE-70 | |
| | Mean | sd | Mean | sd | Mean | sd |
| 4a | 80.86 | 5.00 | 99.86 | 3.34 | 77.54 | 4.58 |
| 4b | 99.05 | 9.73 | 100.02 | 2.13 | 74.87 | 3.00 |
| 4c | 53.63 | 15.80 | 86.36 | 3.41 | 65.77 | 8.01 |
| 4d | 47.97 | 16.44 | 65.49 | 7.76 | 67.46 | 10.05 |
| 4e | 49.93 | 11.69 | 84.54 | 6.23 | 65.53 | 5.11 |
| 4f | 64.86 | 17.41 | 95.82 | 2.24 | 62.30 | 10.58 |
| 4g** | 86.33 | 16.49 | 100.85 | 0.68 | 81.77 | 5.93 |
| 4h | 98.19 | 4.40 | 104.53 | 4.19 | 100.16 | 3.83 |
| 4i | 78.20 | 25.23 | 93.63 | 5.14 | 79.24 | 21.34 |
| 4j | 101.23 | 19.05 | 104.53 | 4.95 | 91.47 | 5.12 |
| 4k* | 92.22 | 14.23 | 89.70 | 3.89 | 90.05 | 1.44 |
| 4l | 79.09 | 20.73 | 103.81 | 13.20 | 98.85 | 12.38 |
| 4m | 55.90 | 11.59 | 91.31 | 10.11 | 84.71 | 13.96 |
| 4n | 39.38 | 7.50 | 80.94 | 23.98 | 75.20 | 22.27 |
| 4o | 54.85 | 13.28 | 90.09 | 6.90 | 74.06 | 6.12 |
| 4p | 49.75 | 13.06 | 96.33 | 10.31 | 72.12 | 5.30 |
| 5b | 77.53 | 18.86 | 104.02 | 8.37 | 77.57 | 4.46 |

TABLE 3-continued

Table 3: Proliferation of tumor cell lines after incubation with various indeno[1,2-b]indoles

| Compound | T/C (%) 5637 Mean | sd | SISO Mean | sd | KYSE-70 Mean | sd |
|---|---|---|---|---|---|---|
| 5c | 58.02 | 7.63 | 94.16 | 4.84 | 74.80 | 5.80 |
| 5j** | 104.23 | | 114.84 | | 90.07 | |
| 5n | 19.81 | 23.69 | 59.42 | 27.96 | 41.13 | 25.86 |
| 6b | −1.73 | 1.07 | 0.28 | 1.50 | 1.26 | 3.50 |
| 6c | 0.44 | 0.41 | 5.30 | 2.61 | 12.05 | 4.90 |
| 6d* | 69.73 | 2.62 | 87.25 | 2.86 | 92.00 | 10.39 |

1. All substances were tested at 20 μM, with the following exceptions:
2. *= 5 μM
3. **= 10 μM
Substances marked in blue were investigated further.

TABLE 4

$IC_{50}$ values of the inhibition of cell proliferation of selected indeno[1,2-b]indoles for various tumor cell lines

| Compound | 5637 | | SISO | | KYSE-70 | | MCF-7 | | DAN-G | | LCLC | | A427 | | RT-4 | |
|---|---|---|---|---|---|---|---|---|---|---|---|---|---|---|---|---|
| | Mean | sd | Mean | sd | Mean | sd | Mean | sd | Mean | sd | Mean | sd | Mean | sd | Mean | sd |
| 4d | 10.71 | 5.01 | 12.26 | 2.28 | >20 | | 6.53 | 1.44 | >20 | | 5.66 | 2.94 | >20 | | >20 | |
| 6b | 1.67 | 0.40 | 1.54 | 0.17 | 1.54 | 0.36 | 1.32 | 0.07 | >10 | | 1.47 | 0.19 | 1.40 | 0.22 | >10 | |
| 6c | 2.75 | 0.59 | 2.82 | 0.56 | 2.83 | 0.30 | 3.27 | 0.40 | >20 | | 4.14 | 1.00 | 3.74 | 0.65 | >20 | | sd = standard deviation

TABLE 5

Table 5: IC50 values [μM] of selected indeno[1,2-b]indoles on various human protein kinases

| Substance | AKT1 | ARK5 | Aurora-A | Aurora-B | B-RAF-VE | CDK2/CycA | CDK4/CycD1 | CK2-alpha1 |
|---|---|---|---|---|---|---|---|---|
| 4b | >10 | >10 | >10 | >10 | >10 | >10 | >10 | 7.8 |
| 6b | 9.3 | 0.17 | 5.8 | 5.4 | >10 | >10 | >10 | >10 |
| 6c | >10 | 1.3 | >10 | >10 | >10 | >10 | 7.6 | >10 |

| Substance | EGF-R | EPHB4 | FAK | ERBB2 | IGF1-R | SRC | VEGF-R2 | VEGF-R3 |
|---|---|---|---|---|---|---|---|---|
| 4b | >10 | >10 | >10 | >10 | >10 | >10 | >10 | >10 |
| 6b | >10 | >10 | >10 | >10 | 2.9 | 1.6 | 1.9 | 0.96 |
| 6c | 2.5 | 9.3 | >10 | 7.6 | 2.5 | 0.8 | 3.3 | 7.5 |

| Substance | FLT3 | INS-R | MET | PDGFR-beta | PLK1 | SAK | TIE2 | COT |
|---|---|---|---|---|---|---|---|---|
| 4b | >10 | >10 | >10 | >10 | >10 | >10 | >10 | >10 |
| 6b | 0.051 | 1.6 | >10 | >10 | >10 | 1.7 | 3.2 | 9.3 |
| 6c | 9.2 | 6.5 | >10 | >10 | >10 | 3.9 | 4.7 | 4.4 |

LITERATURE

1. Buchanan, S. G., Protein structure: discovering selective protein kinase inhibitors. *Targets* 2003, 2, (3), 101-108.
2. Litchfield, D. W., Protein kinase CK2: structure, regulation and role in cellular decisions of life and death. *Biochem J* 2003, 369, (Pt 1), 1-15.
3. Bibby, A. C.; Litchfield, D. W., The Multiple Personalities of the Regulatory Subunit of Protein Kinase CK2: CK2 Dependent and CK2 Independent Roles Reveal a Secret Identity for CK2beta. *Int J Biol Sci* 2005, 1, (2), 67-79.
4. Meggio, F.; Pinna, L. A., One-thousand-and-one substrates of protein kinase CK2beta *Faseb J* 2003, 17, (3), 349-68.
5. Pepperkok, R.; Lorenz, P.; Ansorge, W.; Pyerin, W., Casein kinase II is required for transition of G0/G1, early G1, and G1/S phases of the cell cycle. *J Biol Chem* 1994, 269, (9), 6986-91.
6. Pepperkok, R.; Lorenz, P.; Jakobi, R.; Ansorge, W.; Pyerin, W., Cell growth stimulation by EGF: inhibition through antisense-oligodeoxynucleotides demonstrates important role of casein kinase II. *Exp Cell Res* 1991, 197, (2), 245-53.
7. Lorenz, P., Pepperkok, R.; Ansorge, W.; Pyerin, W., Cell biological studies with monoclonal and polyclonal antibodies against human casein kinase II subunit beta demonstrate participation of the kinase in mitogenic signaling. *J Biol Chem* 1993, 268, (4), 2733-9.
8. Wang, G.; Ahmad, K. A.; Ahmed, K., Role of protein kinase CK2 in the regulation of tumor necrosis factor-related apoptosis inducing ligand-induced apoptosis in prostate cancer cells. *Cancer Res* 2006, 66, (4), 2242-9.
9. Tawfic, S.; Yu, S.; Wang, H.; Faust, R.; Davis, A.; Ahmed, K., Protein kinase CK2 signal in neoplasia. *Histol Histopathol* 2001, 16, (2), 573-82.

10. Hessenauer, A.; Montenarh, M.; Gotz, C., Inhibition of CK2 activity provokes different responses in hormone-sensitive and hormone-refractory prostate cancer cells. *Int J Oncol* 2003, 22, (6), 1263-70.
11. Yenice, S.; Davis, A. T.; Goueli, S. A.; Akdas, A.; Limas, C.; Ahmed, K., Nuclear casein kinase 2 (CK-2) activity in human normal, benign hyperpastic, and cancerous prostate. *Prostate* 1994, 24, (1), 11-6.
12. Landesman-Bollag, E.; Romieu-Mourez, R.; Song, D. H.; Sonenshein, G. E.; Cardiff, R. D.; Seldin, D. C., Protein kinase CK2 in mammary gland tumorigenesis. *Oncogene* 2001, 20, (25), 3247-57.
13. Daya-Makin, M.; Sanghera, J. S.; Mogentale, T. L.; Lipp, M.; Parchomchuk, J.; Hogg, J. C.; Pelech, S. L., Activation of a tumor-associated protein kinase (p40TAK) and casein kinase 2 in human squamous cell carcinomas and adenocarcinomas of the lung. *Cancer Res* 1994, 54, (8), 2262-8.
14. Faust, R. A.; Gapany, M.; Tristani, P.; Davis, A.; Adams, G. L.; Ahmed, K., Elevated protein kinase CK2 activity in chromatin of head and neck tumors: association with malignant transformation. *Cancer Lett* 1996, 101, (1), 31-5.
15. ole-MoiYoi, O. K.; Brown, W. C.; Tams, K. P.; Nayar, A.; Tsukamoto, T.; Macklin, M. D., Evidence for the induction of casein kinase II in bovine lymphocytes transformed by the intracellular protozoan parasite Theileria parva. *Embo J* 1993, 12, (4), 1621-31.
16. Seldin, D. C.; Leder, P., Casein kinase II alpha transgene-induced murine lymphoma: relation to theileriosis in cattle. *Science* 1995, 267, (5199), 894-7.
17. Scaglioni, P. P.; Yung, T. M.; Cai, L. F.; Erdjument-Bromage, H.; Kaufman, A. J.; Singh, B.; Teruya-Feldstein, J.; Tempst, P.; Pandolfi, P. P., A CK2-dependent mechanism for degradation of the PML tumor suppressor. *Cell* 2006, 126, (2), 269-83.
18. Sarno, S.; Ruzzene, M.; Frascella, P.; Pagano, M. A.; Meggio, F.; Zambon, A.; Mazzorana, M.; Di Maira, G.; Lucchini, V.; Pinna, L. A., Development and exploitation of CK2 inhibitors. *Mol Cell Biochem* 2005, 274, (1-2), 69-76.
19. Sarno, S.; Salvi, M.; Battistutta, R.; Zanotti, G.; Pinna, L. A., Features and potentials of ATP-site directed CK2 inhibitors. *Biochim Biophys Acta* 2005, 1754, (1-2), 263-70.
20. Yim, H.; Lee, Y. H.; Lee, C. H.; Lee, S. K., Emodin, an anthraquinone derivative isolated from the rhizomes of Rheum palmatum, selectively inhibits the activity of casein kinase II as a competitive inhibitor. *Planta Med* 1999, 65, (1), 9-13.
21. Sarno, S.; Reddy, H.; Meggio, F.; Ruzzene, M.; Davies, S. P.; Donella-Deana, A.; Shugar, D.; Pinna, L. A., Selectivity of 4,5,6,7-tetrabromobenzotriazole, an ATP site-directed inhibitor of protein kinase CK2 ('casein kinase-2'). *FEBS Lett* 2001, 496, (1), 44-8.
22. Pagano, M. A.; Meggio, F.; Ruzzene, M.; Andrzejewska, M.; Kazimierczuk, Z.; Pinna, L. A., 2-dimethylamino-4,5,6,7-tetrabromo-1H-benzimidazole: a novel powerful and selective inhibitor of protein kinase CK2. *Biochem Biophys Res Commun* 2004, 321, (4), 1040-4.
23. Sarno, S.; de Moliner, E.; Ruzzene, M.; Pagano, M. A.; Battistutta, R.; Bain, J.; Fabbro, D.; Schoepfer, J.; Elliott, M.; Furet, P.; Meggio, F.; Zanotti, G.; Pinna, L. A., Biochemical and three-dimensional-structural study of the specific inhibition of protein kinase CK2 by [5-oxo-5,6-dihydroindolo(1,2-a)quinazolin-7-yl]acetic acid (IQA) *Biochem J* 2003, 374, (Pt 3), 639-46.
24. Cozza, G.; Bonvini, P.; Zorzi, E.; Poletto, G.; Pagano, M. A.; Sarno, S.; Donella-Deana, A.; Zagotto, G.; Rosolen, A.; Pinna, L. A.; Meggio, F.; Moro, S., Identification of ellagic acid as potent inhibitor of protein kinase CK2: a successful example of a virtual screening application. *J Med Chem* 2006, 49, (8), 2363-6.
25. Guerra, B.; Gotz, C.; Wagner, P.; Montenarh, M.; Issinger, O. G., The carboxy terminus of p53 mimics the polylysine effect of protein kinase CK2-catalyzed MDM2 phosphorylation. *Oncogene* 1997, 14, (22), 2683-8.
26. Yamada et al, *PNAS* 2005, 102:7736-7741
27. Schneider et al., *LUPUS* 2007, 16:221-226
28. Bracht et al. *Anti-Cancer Drugs* 2006, 17:41-51
29. Hemmerling et al. *Z. Naturforsch.* 59B, 2006, 1143-1152

The invention claimed is:
1. A compound of structure I, structure IA or structure II:

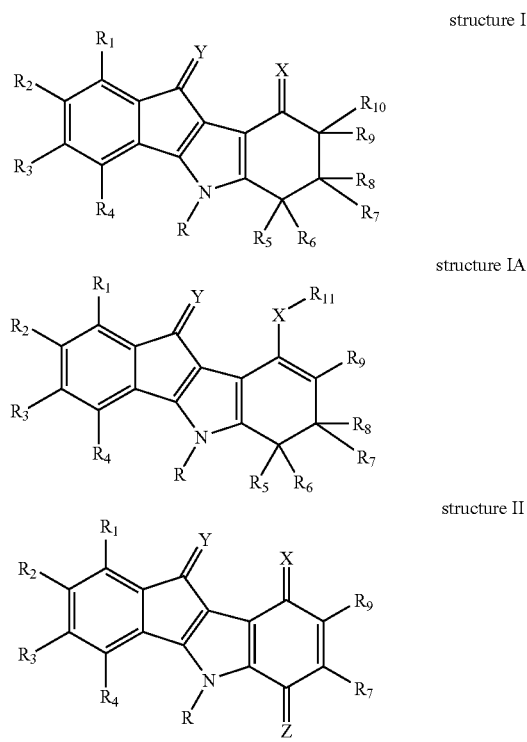

wherein:
R represents
 a hydrogen atom or
 a straight or branched chain $C_1$-$C_8$-alkyl group or
 a $C_3$-$C_8$-cycloalkyl group or
 a straight or branched chain $C_2$-$C_8$-alkenyl group or
 a $C_3$-$C_8$-cycloalkenyl group or
 an aryl group or
 a heteroaryl group or
 an aryl-$C_1$-$C_8$-alkyl group or
 a heteroaryl-$C_1$-$C_8$-alkyl group,
wherein R is optionally mono- or polysubstituted, identically or differently substituted by
 hydroxy groups or
 cyano groups or
 nitro groups or
 halogen atoms or
 carboxy groups or
 sulfonic acid groups or groups of formula $COOR_{12}$ (alkoxycarbonyl group) or $SO_2OR_{13}$ (alkoxy sulfonic acid group), wherein each of $R_{12}$, $R_{13}$, which are identical or different, is a straight or branched chain $C_1$-$C_8$-alkyl group or $C_3$-$C_8$-cycloalkyl group or a straight or branched $C_2$-$C_8$-alkenyl group, in each case optionally mono- or polysubstituted identically or differently substituted by hydroxy groups, cyano groups, nitro groups, halogen atoms, carboxy groups, or groups of the formulae $NR_{14}R_{15}$, $CONR_{14}R_{15}$, and $CSNR_{14}R_{15}$, $SO_2NR_{14}R_{15}$, wherein each of $R_{14}$, $R_{15}$ which are identical or different, is a hydrogen atom or a straight or branched $C_1$-$C_8$-alkyl group or a $C_3$-$C_8$-cycloalkyl group, or $R_{14}$, $R_{15}$ together with the nitrogen atom to which they are attached form a nitrogen-containing heterocycle, or groups of the formulae $CONR_{16}R_{17}$ (carboxamide group), $CSNR_{16}R_{17}$ (thiocarboxamide group), and $SO_2NR_{16}R_{17}$ (sulfonamide groups), wherein each of $R_{16}$, $R_{17}$ which are identical or different, is a hydrogen atom or a straight or branched chain $C_1$-$C_8$-alkyl group or $C_3$-$C_8$-cycloalkyl group or a straight or branched chain $C_2$-$C_8$-alkenyl group or $R_{16}$, $R_{17}$ together with the nitrogen atom to which they are attached form a nitrogen-containing heterocycle, in each case optionally mono- or polysubstituted identically or differently substituted by hydroxy groups, cyano groups, nitro groups, halogen atoms, carboxy groups, or amino groups $NR_{18}R_{19}$, wherein each of $R_{18}R_{19}$ which are identical or different, is a hydrogen atom or a straight or branched chain $C_1$-$C_8$-alkyl group or $C_3$-$C_8$-cycloalkyl group or straight or branched chain $C_2$-$C_8$-alkenyl group or $R_{18}R_{19}$ together with the nitrogen atom to which they are attached form a nitrogen-containing heterocycle, or acyloxy groups $OCOR_{20}$, wherein $R_{20}$ is a straight or branched chain $C_1$-$C_8$-alkyl group or $C_3$-$C_8$-cycloalkyl group or a straight or branched chain $C_2$-$C_8$-alkenyl group, which in each case is optionally identically or differently substituted, mono- or polysubstituted by hydroxy groups, cyano groups, nitro groups, halogen atoms, carboxy groups, or groups of formulae $COOR_{21}$, $NR_{21}R_{22}$, $CONR_{21}R_{22}$, $CSNR_{21}R_{22}$, and $SO_2NR_{21}R_{22}$, wherein each of $R_{21}$, $R_{22}$, which are identical or different, is a hydrogen atom or a straight or branched chain $C_1$-$C_8$-alkyl group or a $C_3$-$C_8$-cycloalkyl group or $R_{21}$, $R_{22}$ together with the nitrogen to which they are attached form a nitrogen-containing heterocycle, or groups of formula $OR_{23}NR_{24}R_{25}$ (aminoalkyloxy), wherein $R_{23}$ is a straight or branched chain $C_1$-$C_8$-alkyl group, each of $R_{24}$, $R_{25}$, which are identical or different, is a hydrogen atom or a straight or branched chain $C_1$-$C_8$-alkyl group or a $C_3$-$C_8$-cycloalkyl group or $R_{24}$, $R_{25}$ together with the nitrogen atom to which they are attached, form a nitrogen-containing heterocycle;

each of $R_1$, $R_2$, $R_3$, $R_4$, $R_5$, $R_6$, $R_7$, $R_8$, $R_9$, $R_{10}$, which are identical or different, are independently from each other a hydrogen atom or
a straight or branched chain $C_1$-$C_8$-alkyl group or
a $C_3$-$C_8$-cycloalkyl group or
a straight or branched chain $C_2$-$C_8$-alkenyl group or
a $C_3$-$C_8$-cycloalkenyl group or
an aryl group or
a straight or branched chain aryl-$C_1$-$C_8$-alkyl group or
a heteroaryl group or a hydroxy group or
a straight or branched chain $C_1$-$C_8$-alkoxy group or
a $C_3$-$C_8$-cycloalkoxy group or
a straight or branched chain $C_2$-$C_8$-alkenyloxy group or
a $C_3$-$C_8$-cycloalkenyloxy group or
a $C_1$-$C_2$-alkylenedioxy group, which forms one of the groups $R_1$-$R_{10}$ with an adjacent group $R_1$-$R_{10}$, or
an acyloxy group $OCOR_{26}$, wherein $R_{26}$ is a straight or branched chain $C_1$-$C_8$-alkyl group or a straight or branched chain $C_2$-$C_8$-alkenyl group or a $C_3$-$C_8$-cycloalkyl group, or a straight or branched chain aryl-$C_1$-$C_8$-alkoxy group or
an alkoxycarbonylalkyl group $R_{27}COOR_{28}$, wherein each of $R_{27}$, $R_{28}$, which are identical or different, is a straight or branched chain $C_1$-$C_8$-alkyl group or a $C_3$-$C_8$-cycloalkyl group or a straight or branched chain $C_2$-$C_8$-alkenyl group, or a carboxy group, COOH, or
a group of formulae $CONR_{29}R_{30}$ (carboxamide group), $CSNR_{29}R_{30}$ (thiocarboxamide group), and $SO_2NR_{29}R_{30}$ (sulfonamide group), wherein each of $R_{29}$, $R_{30}$, which are identical or different, is a hydrogen atom or a straight or branched chain $C_1$-$C_8$-alkyl group or $C_3$-$C_8$-cycloalkyl group or $R_{29}$, $R_{30}$ together with the nitrogen atom to which they are attached form a nitrogen-containing heterocycle, or
an alkoxycarbonyl group $COOR_{31}$, wherein $R_{31}$ is a straight or branched chain $C_1$-$C_8$-alkyl group or a $C_3$-$C_8$-cycloalkyl group or a straight or branched chain $C_2$-$C_8$-alkenyl group, or
an amino group $NR_{32}R_{33}$, wherein each of $R_{32}$, $R_{33}$, which are identical or different, is a hydrogen atom or a straight or branched chain $C_1$-$C_8$-alkyl group or $C_3$-$C_8$-cycloalkyl group, a straight or branched chain $C_2$-$C_8$-alkenyl group or $R_{32}$, $R_{33}$ together with the nitrogen atom to which they are attached form a nitrogen-containing heterocycle, or
an aminoalkyloxy group of formula $OR_{34}NR_{35}R_{36}$, wherein $R_{34}$ is a straight or branched chain $C_1$-$C_8$-alkyl group or a $C_3$-$C_8$-cycloalkyl group or a straight or branched chain $C_2$-$C_8$-alkenyl group, and each of $R_{35}$, $R_{36}$, which are identical or different, is a hydrogen atom or a straight or branched chain $C_1$-$C_8$-alkyl group or $C_3$-$C_8$-cycloalkyl group, or $R_{35}$, $R_{36}$ together with the nitrogen atom to which they are attached form a nitrogen-containing heterocycle, wherein each of the groups $R_1$, $R_2$, $R_3$, $R_4$, $R_5$, $R_6$, $R_7$, $R_8$, $R_9$, $R_{10}$ is optionally mono- or polysubstituted, identically or differently independently from each other substituted by hydroxy groups or
cyano groups or
nitro groups or
halogen atoms or
carboxy groups or
sulfonic acid groups or
aryl group or
heteroaryl group or
groups of formulae $COOR_{37}$, $NR_{37}R_{38}$, $CONR_{37}R_{38}$ (carboxamide group), $CSNR_{37}R_{38}$ (thiocarboxamide group), and $SO_2NR_{37}R_{38}$ (sulfonamide group), wherein each of $R_{37}$, $R_{38}$ which are identical or different is a hydrogen atom or a straight or branched chain $C_1$-$C_8$-alkyl group or a $C_3$-$C_8$-cycloalkyl group or $R_{37}$, $R_{38}$ together with the nitrogen atom to which they are attached form a nitrogen-containing heterocycle, optionally mono- or poly-substituted identically or differently substituted by hydroxy groups, cyano groups, nitro groups, halogen atoms, carboxy groups or groups of formulae $COOR_{39}$, $NR_{39}R_{40}$, $CONR_{39}R_{40}$, $CSNR_{39}R_{40}$, and $SO_2NR_{39}R_{40}$, wherein each of $R_{39}$, $R_{40}$, which are identical or different, is a hydrogen atom or a straight or branched chain $C_1$-$C_8$-alkyl group or a $C_3$-$C_8$-cycloalkyl group or $R_{39}$, $R_{40}$ together with the nitrogen atom to which they are attached form a nitrogen-containing heterocycle, wherein each of X, Y, Z, which are identical or different, are independently from each other
an oxygen atom,
an imino function $NR_{41}$, wherein $R_{41}$ is a hydrogen atom or a straight or branched chain $C_1$-$C_8$-alkyl group or a $C_3$-$C_8$-cycloalkyl group or a straight or branched chain $C_2$-$C_8$-alkenyl group or a $C_3$-$C_8$-cycloalkenyl group or an aryl group or heteroaryl group, or
an alkyloxyimino function $NOR_{42}$, wherein $R_{42}$ is a hydrogen atom or a straight or branched chain $C_1$-$C_8$-alkyl group or a $C_3$-$C_8$-cycloalkyl group or a straight or branched chain $C_2$-$C_8$-alkenyl group or a $C_3$-$C_r$-cycloalkenyl group, or
an aryloxyimino function $NOR_{43}$, wherein $R_{43}$ is an aryl group or heteroaryl group,
wherein $NR_{41}$, $NOR_{42}$ and $NOR_{43}$, are each optionally mono- or polysubstituted, identically or differently independently from each other substituted by aryl groups, heteroaryl groups, hydroxy groups, cyano groups, nitro groups, halogen atoms or by groups of formulae $COOR_{44}$, $NR_{44}R_{45}$ (amino group), $CONR_{44}R_{45}$ (carboxamide group), $CSNR_{44}R_{45}$ (thiocarboxamide group), and $SO_2NR_{44}R_{45}$ (sulfonamide group), wherein each of $R_{44}$, $R_{45}$, which are identical or different, is a hydrogen atom or a straight or branched chain $C_1$-$C_8$-alkyl group or a $C_3$-$C_8$-cycloalkyl group, or $R_{44}$, $R_{45}$ together with the nitrogen atom to which they are attached form a nitrogen-containing heterocycle,
wherein X—$R_{11}$ in structure IA is
a hydroxy group or
an alkoxy group O—$R_{11}$, wherein $R_{11}$ is a straight or branched chain $C_1$-$C_8$-alkyl group or a $C_3$-$C_8$-cycloalkyl group or a straight or branched chain $C_2$-$C_8$-alkylene group, which in each case is optionally mono- or polysubstituted by aryl groups, heteroaryl groups, hydroxy groups, cyano groups, nitro groups, halogen atoms, carboxy groups or groups of formulae $COOR_{46}$, $NR_{46}R_{47}$, $CONR_{46}R_{47}$, $CSNR_{46}R_{47}$, and $SO_2NR_{46}R_{47}$ wherein each of $R_{46}$, $R_{47}$ which are identical or different, is a hydrogen atom or a straight or branched chain $C_1$-$C_8$-alkyl group or a $C_3$-$C_8$-cycloalkyl group or $R_{46}$, $R_{47}$ together with the nitrogen atom to which they are attached form a nitrogen-containing heterocycle, or
an acyloxy group $OCOR_{48}$, wherein $R_{48}$ is a straight or branched chain $C_1$-$C_8$-alkyl group or a straight or branched chain $C_2$-$C_8$-alkenyl group or a $C_3$-$C_8$-cycloalkyl group or an aryl group or a heteroaryl group, which in each case optionally mono- or polysubstituted by aryl groups, heteroaryl groups, hydroxy groups, cyano groups, nitro groups, halogen atoms, carboxy groups or groups of formulae $COOR_{49}$, $NR_{49}R_{50}$, $CONR_{49}R_{50}$, $CSNR_{49}R_{50}$, and $SO_2NR_{49}R_{50}$, wherein each of $R_{49}$, $R_{50}$, which may be identical or different, is a hydrogen atom or a straight or branched chain $C_1$-$C_8$-alkyl group or a $C_3$-$C_8$-cycloalkyl group or $R_{49}$, $R_{50}$ together with the nitrogen atom to which they are attached form a nitrogen-containing heterocycle, wherein $C_2$-$C_8$-alkenyl groups independently from each other are defined as straight or branched chain hydrocarbon chains having at least one double bond up to the maximum number of conjugated double bonds, and
wherein $C_3$-$C_8$-cycloalkenyl groups independently from each other are defined as cyclic hydrocarbons having at least one double bond up to the maximum number of conjugated double bonds, and
wherein aryl groups independently from each other are defined as phenyl or naphthyl groups, which may be substituted with one or more identical or different substituents such as linear or branched chain $C_1$-$C_8$-alkyl groups, $C_3$-$C_8$-cycloalkylgroups, phenyl-$C_1$-$C_8$-alkyl group, naphthyl-$C_1$-$C_8$-alkyl group, $C_1$-$C_2$-alkylenedioxy group, hydroxy group, nitro group, cyano group, halogen atoms, linear or branched chain $C_1$-$C_8$-alkoxy groups, phenoxy group, linear or branched chain $C_1$-$C_8$-alkoxycarbonyl groups, carboxy group, groups of formulae $OCR_{51}NR_{52}R_{53}$ (amino-$C_1$-$C_8$-alkoxy group), $NR_{52}R_{53}$ (thiocarboxamide group), $CONR_{52}R_{53}$ (carboxamide group), $CSNR_{52}R_{53}$ (thiocarboxamide group), and $SO_2NR_{52}R_{53}$ (sulfonamide group), wherein $R_{51}$ is a linear or branched chain $C_1$-$C_8$-alkyl group, and each of $R_{52}$, $R_{53}$, which are identical or different, is a hydrogen atom or a linear or branched chain $C_1$-$C_8$-alkyl group or a $C_3$-$C_8$-cycloalkyl group or $R_{52}$, $R_{53}$ together with the nitrogen atom to which they are attached form a nitrogen-containing heterocycle,
wherein heteroaryl groups independently from each other are defined as aromatic mono- or bicyclic 5 to 12 membered ring systems containing 1-3 hetero atoms (O, N, S), which may be substituted with one or more identical or different substituents such as linear or branched chain $C_1$-$C_8$-alkyl groups, $C_3$-$C_8$-cycloalkyl groups, linear or branched chain $C_1$-$C_8$-alkylene groups, aryl groups, hydroxy groups, nitro groups, cyano groups, halogen atoms, linear or branched chain $C_1$-$C_8$-alkoxy groups, $C_3$-$C_8$-cycloalkoxy groups, phenoxy groups, groups of formulae $OCR_{54}NR_{55}R_{56}$ (amino-$C_1$-$C_8$-alkoxy group), $NR_{55}R_{56}$ (amino group), $CONR_{55}R_{56}$ (carboxamide group), $CSNR_{55}R_{56}$ (thiocarboxamide group), and $SO_2NR_{55}R_{56}$ (sulfonamide group), wherein $R_{54}$ is a straight or branched chain $C_1$-$C_8$-alkyl group, and each of $R_{55}$, $R_{56}$, which may be identical or different, is a hydrogen atom or a straight or branched chain $C_1$-$C_8$-alkyl group or a $C_3$-$C_8$-cycloalkyl group or $R_{55}$, $R_{56}$ together with the nitrogen atom to which they are attached form a nitrogen-containing heterocycle, and
wherein nitrogen-containing heterocycle independently from each other are defined as a saturated 5-7 membered monocycle, which in addition to nitrogen further contains 1-3 heteroatoms,
or a salt thereof with a pharmaceutically acceptable acid,
or a mixture of isomers, or a pure isomer thereof, wherein isomers are optical isomers and geometric isomers with regard to double bonds.

2. The compound according to claim 1, wherein R is
a hydrogen atom or
a straight or branched chain $C_1$-$C_8$-alkyl group or
a $C_3$-$C_8$-cycloalkyl group or
a straight or branched chain $C_2$-$C_8$-alkenyl group or
a $C_3$-$C_8$-cycloalkenyl group or
an aryl group or
a heteroaryl group, or an amino group NR$_{32}$R$_{33}$, or a straight or branched chain C$_1$-C$_8$-alkoxy group or a C$_3$-C$_8$-cycloalkoxy group, which in each case are optionally substituted as defined in claim 1.

3. The compound according to claim 1, wherein R$_1$, R$_2$, R$_3$, R$_1$, R$_5$, R$_6$, R$_7$, R$_8$, R$_9$, R$_{10}$ which are identical or different, independently from each other are:

a hydrogen atom or a straight or branched chain C$_1$-C$_8$-alkyl group or a C$_3$-C$_8$-cycloalkyl group or a straight or branched chain C$_2$-C$_8$-alkenyl group or a C$_3$-C$_8$-cycloalkenyl group or an aryl group or a heteroaryl group or a hydroxy group or an acyloxy group OCOR$_{26}$, a carboxy group COOH, or an amino group NR$_{32}$R$_{33}$, or a straight or branched chain C$_1$-C$_8$-alkoxy group or a C$_1$-C$_2$-alkylenedioxy group, which in each case are optionally substituted as defined in claim 1.

4. The compound according to claim 1, wherein X is an oxygen atom.

5. The compound according to claim 1, wherein Y is an oxygen atom.

6. The compound according to claim 1, wherein Z is an oxygen atom.

7. The compound according to claim 1, wherein X and Y are each oxygen.

8. The compound according to claim 1, wherein R$_5$-R$_{10}$ are each hydrogen.

9. The compound according to claim 1, wherein X, Y and Z are each oxygen.

10. The compound according to claim 1, wherein R$_7$ and R$_9$ are each hydrogen.

11. The compound according to claim 1, wherein R$_1$-R$_{10}$ are identical or different and are each hydrogen, straight or branched chain C$_1$-C$_8$-alkyl groups or straight or branched chain C$_1$-C$_8$-alkoxy groups.

12. The compound according to claim 1, wherein R is a hydrogen atom or a straight or branched chain C$_1$-C$_8$-alkyl group or an aryl group or a straight or branched aryl-C$_1$-C$_8$-alkyl group.

13. The compound according to claim 1 having the structure I and being designated as 5-isopropyl-5,6,7,8-tetrahydro-indeno[1,2-b]indole-9, 10-dione according to IUPAC, or a salt of said compound with a pharmaceutically acceptable acid.

14. The compound according to claim 1 having the structure I and being designated as 5-phenethyl-5,6,7,8-tetrahydro-indeno[1,2-b]indole-9, 10-dione according to EUPAC or a salt of said compound with a pharmaceutically acceptable acid.

15. The compound according to claim 1 having the structure I and being designated as 5-(1-phenyl-ethyl)-5,6,7,8-tetrahydroindeno[1,2-b]indole-9,10-dione according to IIJ-PAC, an isomer thereof, or a salt of said compound with a pharmaceutically acceptable acid.

16. The compound according to claim 1 having the structure I and being designated as 5-phenyl-5,6,7,8-tetrahydro-indeno[1,2-b]indol-9,10-dion, or a salt of said compound with a pharmaceutically acceptable acid.

17. The compound according to claim 1 having the structure II and being designated as 5-isopropyl-5H-indeno[1,2-b]indole-6,9,10-trione according to JUPAC or a salt of said compound with a pharmaceutically acceptable acid.

18. The compound according to claim 1 having the structure II and being designated 5-benzyl-5,6,9,10-tetrahydroindeno[1,2-b]indole-6,9,10-trione according to IUPAC or a salt of said compound with a pharmaceutically acceptable acid.

19. The compound according to claim 1 having the structure II and being designated as 5-phenethyl-5H-indeno[1,2-b]indole-6,9,10-trione according to TUPAC or a salt of said compound with a pharmaceutically acceptable acid.

20. The compound according to claim 1 having the structure IA, wherein XR$_{11}$ is OR$_{11}$ wherein R$_{11}$ is an optionally substituted C$_1$-C$_8$-alkyl group, an aryl group or a heteroaryl group.

21. A method of inhibiting a serine/threonine kinase comprising contacting said serine/threonine kinase with a compound according to claim 1.

22. The method according to claim 21, wherein the kinase is a human serine/threonine kinase.

23. The method according to claim 21, wherein the kinase is CK2 kinase.

24. The method according to claim 21, wherein the inhibition is specific.

25. The method according to claim 21, wherein the compound is used in combination with a further protein kinase inhibiting agent selected from emodin, 4,5,6,7-tetrabromo-1-H-benzotriazole (TBB), 2-dimethylamino-4,5,6,7-tetrabromo-1H-benzimidazole, (5-oxo-5,6-dihydroindolo[1,2-a]quinoxalin-7-yl)acetic acid and ellagic acid.

26. A method of treating cancer selected from breast carcinoma, lung carcinoma, cervix carcinoma, or esophageal carcinoma, comprising administering to the patient an effective amount of a compound according to claim 1.

27. A method for treating an inflammatory disease selected from glomerulonephritis or lupus erythematosus comprising administering to a patient an effective amount of a compound according to claim 1.

28. A diagnostic agent for breast carcinoma, lung carcinoma, cervix carcinoma, or esophageal carcinoma, comprising a compound according to claim 1.

29. A diagnostic agent for glomerulonephritis or lupus erythematosus, comprising a compound according to claim 1.

30. The diagnostic agent according to claim 28, wherein said agent is suitable for the investigation of the role of serine/threonine kinases in cellular processes in pathogenesis or in ontogenesis and in other evolutionary biological processes.

31. The diagnostic agent according to claim 30, wherein the serine/threonine kinase is CK2 protein kinase.

32. The method according to claim 26, wherein said compound is administered in combination with another drug for the treatment of cancer selected from breast carcinoma, lung carcinoma, cervix carcinoma, or esophageal carcinoma.

33. The method according to claim 27, wherein said compound is administered in combination with another drug for the treatment of an inflammatory disease selected from glomerulonephritis or lupus erythematosus.

34. A pharmaceutical preparation comprising at least one compound according to claim 1 as a drug in an effective amount and at least one pharmaceutically acceptable additive or/and an adjuvant.

35. A method for the synthesis of a compound of the structure I according to claim 1, comprising:
(1) preparing a cyclic enaminone 2 from a cyclic 1,3-diketone by reaction with ammonia or/and a primary amine,

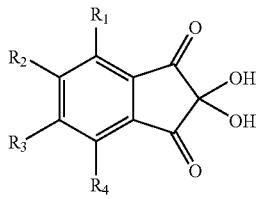

1

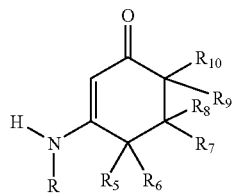

2

(2) reacting the enaminone 2 with compound 1 to obtain addition compound 3, and

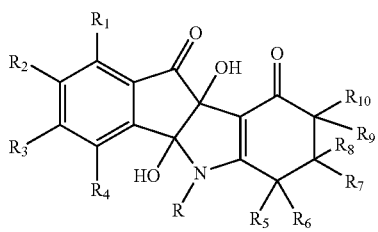

3

(3) deoxygenating compound 3 to obtain compound 4 having structure I,

Structure I

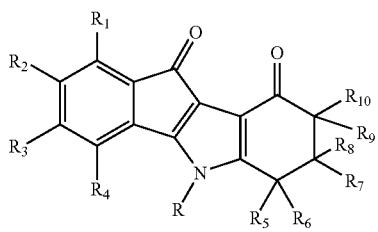

4 wherein $R_5$, $R_6$, $R_8$ and $R_{10}$ are H and R, $R_1$, $R_2$, $R_3$, $R_4$, $R_7$, $R_9$ are as defined and X, Y and Z are oxygen.

36. The method according to claim 35, wherein (3) is carried out with
(a) N,N,N',N'-tetralkyl sulfurous acid diamide with alkyl=methyl or ethyl or
(b) thionylchloride and an organic alkaline substance such as sodium carbonate or an organic base such as trialkyl amine $R_3N$, wherein R is a straight or branched chain $C_1$-$C_8$-alkyl group, in particular methyl or ethyl, or a $C_3$-$C_8$-cycloalkyl group, or a nitrogen-containing aromatic amine such as imidazole or pryridine, or
(c) thionyldiimidazole.

37. A method for the synthesis of a compound of structure II according to claim 1, comprising:
(1) preparing a cyclic enaminone 2 from a cyclic 1,3-diketone by reaction with ammonia or/and a primary amine,

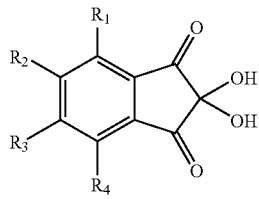

1

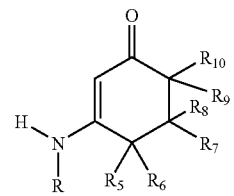

2

(2) reacting the enaminone 2 with compound 1 to obtain addition compound 3, and

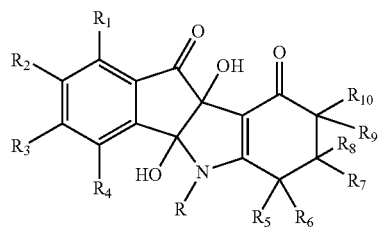

3

(3) deoxygenating compound 3 to obtain compound 4 having structure I,

Structure I

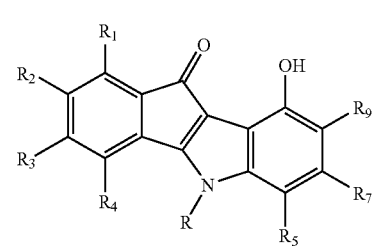

4 wherein $R_5$, $R_6$, $R_8$ and $R_{10}$ are H and R, $R_1$, $R_2$, $R_3$, $R_4$, $R_7$, $R_9$ are as defined and X, Y and Z are oxygen,
(4) dehydrogenating compound 4, to obtain compound 5, and

5

(5) oxidizing compound 5, to obtain compound 6 which has structure II,

Structure II

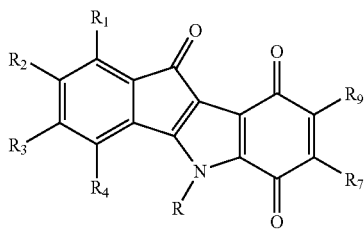

wherein $R_5$, $R_6$, $R_8$ and $R_{10}$ are H and R, $R_1$, $R_2$, $R_3$, $R_4$, $R_7$, $R_9$ are as defined.

38. The method according to claim 37, wherein the dehydrogenation in (4) is carried out with DDQ.

39. The method according to claim 37, wherein the oxidation in (5) is carried out catalytically with oxygen.

40. A method for the synthesis of a compound according to structure I, IA or II according to claim 1, comprising:

(1) preparing a cyclic enaminone 2 from a cyclic 1,3-diketone by reaction with ammonia or/and a primary amine,

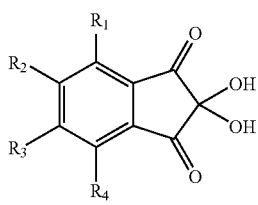

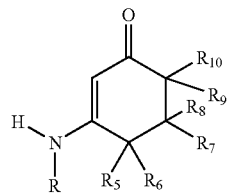

(2) reacting the enaminone 2 with compound 1 to obtain addition compound 3, and

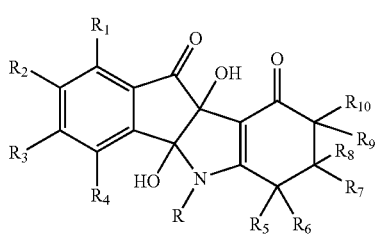

(3) deoxygenating compound 3 to obtain compound 4 having structure I,

Structure I

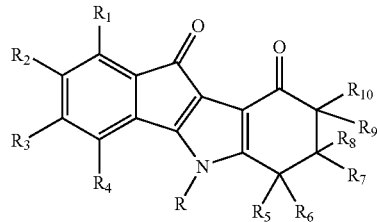

wherein $R_5$, $R_6$, $R_8$ and $R_{10}$ are H and R, $R_1$, $R_2$, $R_3$, $R_4$, $R_7$, $R_9$ are as defined and X, Y and Z are oxygen, and (4) optionally dehydrogenating compound 4, to obtain compound 5, and

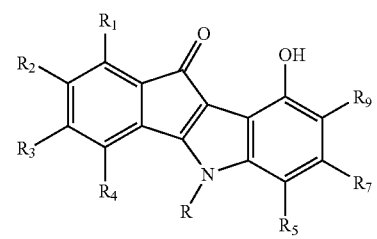

(5) oxidizing compound 5, to obtain compound 6 which has structure II,

Structure II

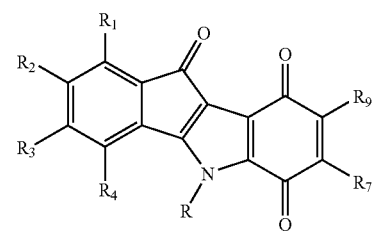

wherein $R_5$, $R_6$, $R_8$ and $R_{10}$ are H and R, $R_1$, $R_2$, $R_3$, $R_4$, $R_7$, $R_9$ are as defined wherein the oxygen groups X, Y or/and Z are converted to $=NR_{41}$, $=NOR_{42}$ or/and $=NOR_{43}$, or (6) optionally subjecting compound 4 to O-alkylation or O-acetylation, to obtain a compound of structure IA.

41. The compound according to claim 1, wherein nitrogen-containing heterocycle independently from each other are defined as a saturated 5-7 membered monocycle, which in addition to nitrogen further contains 1-3 heteroatoms selected from O, N, and S.

42. The compound according to claim 1, wherein nitrogen-containing heterocycle independently from each other are defined as pyrrolidinyl-, piperidyl-, morpholinyl- or piperazinyl.

43. The compound according to claim 1, wherein said pharmaceutically acceptable acid is hydrochloric acid, hydrobromic acid, sulfuric acid, phosphoric acid, acetic acid, trifluoroacetic acid, lactic acid, pyruvic acid, malonic acid, succinic acid, glutaric acid, tartaric acid, citric acid, ascorbic acid, or oxalic acid.

* * * * *

UNITED STATES PATENT AND TRADEMARK OFFICE
CERTIFICATE OF CORRECTION

PATENT NO.        : 8,133,913 B2
APPLICATION NO.   : 12/444349
DATED             : March 13, 2012
INVENTOR(S)       : Hans-Jorg Hemmerling et al.

It is certified that error appears in the above-identified patent and that said Letters Patent is hereby corrected as shown below:

Title page Item (73) Assignee: reads "Heinrich-Heine Universitat Dusseldof," should read -- Heinrich-Heine Universitat Dusseldorf --.

In the Claims

Column 33, Line 22 claim 1 reads: "or branched chain $C_2$-$C_8$-alkenyl group or a $C_3$-Crcy-" should read -- or branched chain $C_2$-$C_8$-alkenyl group or a $C_3$-$C_8$ cy- --

Column 35, Line 54 claim 14 reads: "dro-indeno[1,2-b]indole-9, 10-dione according to EUPAC or" should read -- dro-indeno[1,2-b]indole-9,10-dione according to IUPAC or --

Column 35, Line 59 claim 15 reads: "tetrahydroindeno[1,2-b] indole-9,10-dione according to IIJ-" should read -- tetrahydroindeno[1,2-b] indole-9,10-dione according to IU- --

Column 36, Line 1 claim 18 reads: "b]indole-6,9,10-trione according to JUPAC or a salt of said" should read -- b]indole-6,9,10-trione according to IUPAC or a salt of said --

Column 36, Line 10 claim 19 reads: "b]indole-6,9,10-trione according to TUPAC or a salt of said" should read -- b]indole-6,9,10-trione according to IUPAC or a salt of said --

Signed and Sealed this
Fifteenth Day of September, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,133,913 B2 | |
| APPLICATION NO. | : 12/444349 | |
| DATED | : March 13, 2012 | |
| INVENTOR(S) | : Hans-Jorg Hemmerling et al. | |

It is certified that error appears in the above-identified patent and that said Letters Patent is hereby corrected as shown below:

Title page Item (73) Assignee: reads "Heinrich-Heine Universitat Dusseldof," should read
-- Heinrich-Heine Universitat Dusseldorf --

In the Claims

Column 33, Line 22 claim 1 reads: "or branched chain $C_2$-$C_8$-alkenyl group or a $C_3$-Crcy-" should read
-- or branched chain $C_2$-$C_8$-alkenyl group or a $C_3$-$C_8$ cy- --

Column 35, Line 54 claim 14 reads: "dro-indeno[ 1,2-b]indole-9, 10-dione according to EUPAC or"
should read -- dro-indeno[1,2-b]indole-9,10-dione according to IUPAC or --

Column 35, Line 59 claim 15 reads: "tetrahydroindeno[1,2-b] indole-9,10-dione according to IIJ-"
should read -- tetrahydroindeno[1,2-b] indole-9,10-dione according to IU- --

Column 36, Line 1 claim 17 reads: "b]indole-6,9,10-trione according to JUPAC or a salt of said"
should read -- b]indole-6,9,10-trione according to IUPAC or a salt of said --

Column 36, Line 10 claim 19 reads: "b]indole-6,9,10-trione according to TUPAC or a salt of said"
should read -- b]indole-6,9,10-trione according to IUPAC or a salt of said --

This certificate supersedes the Certificate of Correction issued September 15, 2015.

Signed and Sealed this
Twenty-first Day of June, 2016

Michelle K. Lee
*Director of the United States Patent and Trademark Office*